United States Patent
Litvak et al.

(10) Patent No.: US 12,251,564 B2
(45) Date of Patent: Mar. 18, 2025

(54) SYSTEMS AND METHODS FOR FITTING A HEARING SYSTEM TO A RECIPIENT BASED ON CORTICAL POTENTIALS OF THE RECIPIENT

(71) Applicant: Advanced Bionics AG, Staefa (CH)

(72) Inventors: Leonid M. Litvak, Los Angeles, CA (US); R. Tissa Karunasiri, Valencia, CA (US); Hannah A. Glick, Ventura, CA (US); Kanthaiah Koka, Valencia, CA (US); Chen Chen, Valencia, CA (US); Jason Galster, Studio City, CA (US)

(73) Assignee: Advanced Bionics AG, Staefa (CH)

(*) Notice: Subject to any disclaimer, the term of this patent is extended or adjusted under 35 U.S.C. 154(b) by 394 days.

(21) Appl. No.: 17/762,971

(22) PCT Filed: Oct. 23, 2020

(86) PCT No.: PCT/US2020/057177
§ 371 (c)(1),
(2) Date: Mar. 23, 2022

(87) PCT Pub. No.: WO2021/081414
PCT Pub. Date: Apr. 29, 2021

(65) Prior Publication Data
US 2022/0339445 A1 Oct. 27, 2022

Related U.S. Application Data

(60) Provisional application No. 62/926,351, filed on Oct. 25, 2019.

(51) Int. Cl.
*A61N 1/36* (2006.01)
*A61N 1/05* (2006.01)
*H04R 25/00* (2006.01)

(52) U.S. Cl.
CPC ....... *A61N 1/36039* (2017.08); *A61N 1/0541* (2013.01); *H04R 25/606* (2013.01)

(58) Field of Classification Search
CPC . A61N 1/36039; A61N 1/0541; H04R 25/606
See application file for complete search history.

(56) References Cited

U.S. PATENT DOCUMENTS 8,818,517 B2 * 8/2014 Faltys ................ A61N 1/36038
607/57
2009/0254149 A1 10/2009 Polak
(Continued)

FOREIGN PATENT DOCUMENTS

| WO | 1998036711 | 8/1998 |
| WO | 2013116161 | 8/2013 |

(Continued)

OTHER PUBLICATIONS

"International Search Report and Written Opinion received on Mar. 18, 2021 in International Application No. PCT/US2020/057177.".

*Primary Examiner* — Brian T Gedeon
(74) *Attorney, Agent, or Firm* — ALG Intellectual Property, LLC

(57) ABSTRACT

An illustrative cochlear implant system includes an electrode lead having an array of electrodes, a cochlear implant coupled with the electrode lead and configured to be implanted within a recipient together with the electrode lead, and a processing unit communicatively coupled to the cochlear implant. The processing unit is configured to direct the cochlear implant to apply stimulation to the recipient by way of the array of electrodes. The processing unit is further configured to detect, by way of one or more electrodes included in the array of electrodes, a cortical potential produced by the recipient. Based on the detected cortical potential, the processing unit is configured to determine a (Continued)

fitting parameter associated with the cochlear implant system. Corresponding systems and methods are also disclosed.

19 Claims, 10 Drawing Sheets

(56) References Cited

U.S. PATENT DOCUMENTS

2017/0340876 A1* 11/2017 Vanpoucke ........ A61N 1/36038
2017/0360365 A1* 12/2017 Heasman ............ A61B 5/4836
2018/0125386 A1*  5/2018 Lim ....................... A61B 5/291
2020/0012346 A1*  1/2020 Schiff .................... A61B 5/383

FOREIGN PATENT DOCUMENTS

| WO | WO-2015142355 A1 * | 9/2015 | ......... A61N 1/36032 |
| WO | 2016057018 | 4/2016 | |
| WO | WO-2016057018 A1 * | 4/2016 | ........... A61N 1/0541 |

* cited by examiner

ND METHODS FOR FITTING A
SYSTEMS AND METHODS FOR FITTING A HEARING SYSTEM TO A RECIPIENT BASED ON CORTICAL POTENTIALS OF THE RECIPIENT

RELATED APPLICATIONS

The present application claims priority under 35 U.S.C. § 119(e) to U.S. Provisional Patent Application No. 62/926,351, filed on Oct. 25, 2019, and entitled "OPTIMIZING A FITTING OF A HEARING SYSTEM TO A RECIPIENT BASED ON A CORTICAL POTENTIAL," the contents of which are hereby incorporated by reference in their entirety.

BACKGROUND INFORMATION

Various types of hearing systems are in use today by hearing system recipients with many different hearing capabilities and challenges. For example, people who are hard of hearing but retain basic hearing capabilities in one or both ears may use a hearing aid system for one or both ears. As another example, people who have little or no natural hearing may benefit from a cochlear implant system that stimulates auditory nerves in ways that natural hearing mechanisms fail to do for various reasons. In some cases, certain cochlear implant recipients may retain partial hearing, such as an ability to hear only certain frequencies. Such recipients may benefit from a hybrid approach offered by electroacoustic hearing systems, which may provide both the acoustic stimulation of a hearing aid system (e.g., for certain frequencies) and the electrical stimulation of a cochlear implant system (e.g., for other frequencies). Certain hearing system recipients may also benefit from use of a bimodal hearing system that employs one type of hearing system (e.g., a hearing aid system) for one ear, and another type of hearing system (e.g., a cochlear implant system or electroacoustic hearing system) for the other ear.

Regardless of which of these or other types of hearing systems a particular recipient may use, it may be desirable for a hearing system to operate in a manner that is catered to the recipient's own unique preferences and characteristics.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
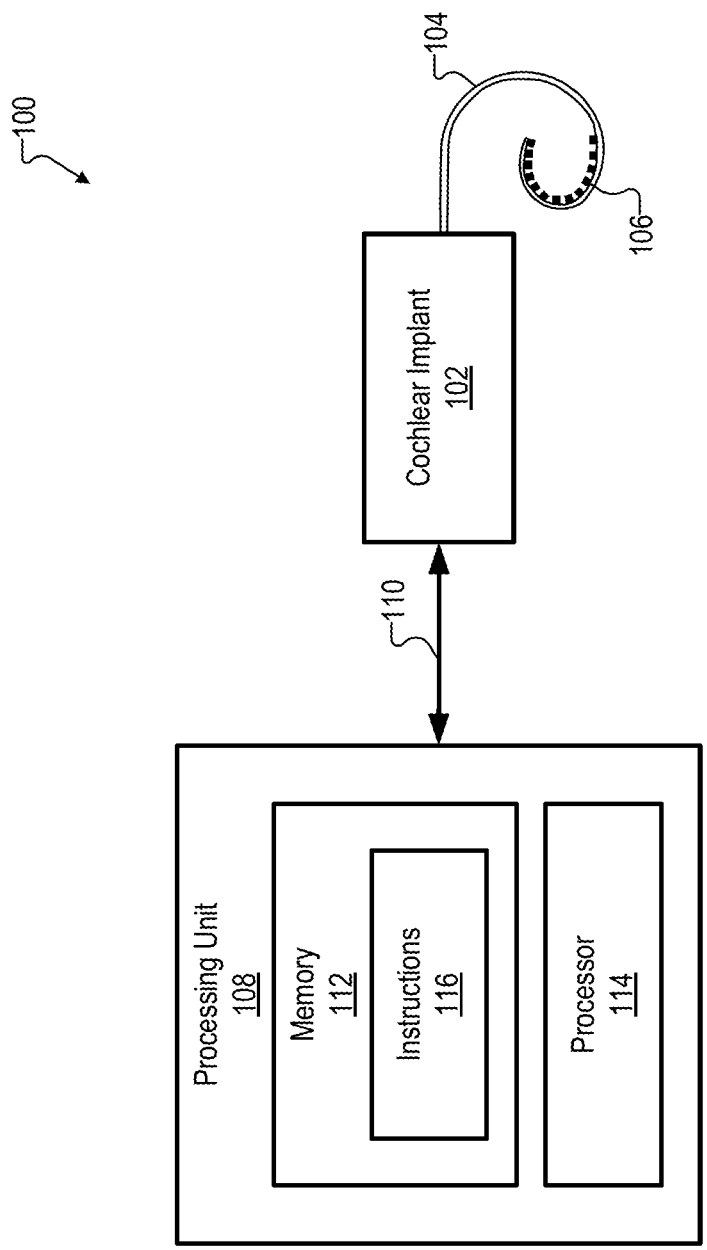
FIG. 1 shows an illustrative cochlear implant system configured to be fitted to a recipient based on cortical potentials of the recipient.

Systems and methods for fitting a hearing system to a recipient based on cortical potentials of the recipient are described herein. As mentioned above, hearing recipients may include people suffering from various types of hearing loss and having various degrees of hearing loss, including different types and/or degrees of hearing loss at each ear. Regardless of what type or degree of hearing loss a particular hearing system recipient may have, it may be desirable for a hearing system used by the recipient to be customized for various unique preferences and/or characteristics of the recipient. The process of customizing a hearing system to preferences and characteristics of a recipient may be referred to as "fitting" the hearing system to the recipient, and may be performed in various ways using a variety of tools, tests, and measurements. For example, certain novel systems and methods for fitting a hearing system to a recipient are described herein as performing the fitting based on cortical potentials of the recipient that may be detected using electrodes integrated with an cochlear implant system.

As will be described in more detail below, cortical potentials of the recipient may refer to various types of neurofeedback detectable from the brain of a hearing system recipient. Voluntarily (i.e., as a result of conscious efforts of the recipient) or involuntarily (i.e., as a result of subconscious brain processes of the recipient), the recipient's brain may produce signals (e.g., brain waves, etc.) that may be detected (e.g., as voltages, currents, and/or other types of signals) by various types of electrodes and/or other suitable sensors. In certain examples, stimulation may be applied to the recipient such that cortical potentials are detected as evoked responses to the stimulation. In other examples, it may be useful to monitor cortical potentials without any particular stimulation being applied to evoke a response. Various types of stimulation and cortical potentials that may be evoked thereby will be described in more detail below.

By detecting and analyzing cortical potentials in certain ways, systems and methods described herein allow for hearing systems to be accurately and efficiently fitted to recipients. These systems and methods may significantly improve hearing system technology and provide technical benefits to hearing and fitting systems, while also providing usability benefits and advantages to recipients, caretakers, clinicians, and other users associated with the hearing systems.

As one illustrative benefit, system and methods configured to rely on cortical potentials (e.g., instead of or together with behavioral feedback and/or other types of feedback obtained from the recipient) when performing fitting procedures may lead to fitting parameters that are highly accurate and objective, fitting sessions that are performed more dynamically and flexibly (e.g., including virtual fitting sessions that will be described below), and improvements in recipient hearing and overall hearing system experience. In particular, systems and methods described herein for fitting a hearing system to a recipient based on cortical potentials may lead to desirable outcomes for recipients who may have difficulty in expressing or articulating their subjective experiences. For example, it may be useful to determine how a recipient's brain responds to different stimuli if the recipient is a small child for whom behavioral feedback or conventional peripheral measurements (electrocochleography ("ECochG"), auditory brainstem responses ("ABRs"), etc.) are unreliable. Similarly, systems and methods described herein may provide significant fitting improvements for recipients with disabilities that affect speech or understanding (e.g., such that the recipients have difficulty in providing verbal or other behavioral feedback), as well as for recipients who suffer from auditory neuropathy.

As another illustrative benefit, systems and methods described herein for fitting hearing systems based on cortical potentials may be performed automatically from time to time without needing to be directed or facilitated by a clinician (e.g., including in virtual fitting sessions when the recipient is not present at a clinic). In some examples, accurate fitting parameters may be determined, updated, and/or adjusted without recipients even needing to be consciously aware that fitting procedures are underway. In this way, fitting parameters may be automatically and dynamically determined and optimized for a variety of different contexts and situations. For example, it may be advantageous for certain fitting parameters to be used when a recipient is in a quiet room and exerting a high degree of focus, and for different fitting parameters to be used when the recipient is in a noisy room, or is asleep or experiencing various other circumstances or hearing contexts.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Systems and methods described herein for fitting a hearing system to a recipient based on cortical potentials of the recipient may provide any of the benefits mentioned above, as well as various additional and/or alternative benefits that will be described and/or made apparent below.

FIG. 1 shows an illustrative cochlear implant system 100 configured to be used by a recipient. Cochlear implant system 100 will be understood to represent one illustrative type of hearing system that may be fitted to a recipient based on cortical potentials in accordance with principles described herein. Additionally, as will be made apparent, cochlear implant system 100 may further serve as an example of a system configured to perform or facilitate methods described herein for fitting hearing systems based on cortical potentials. For instance, an implementation of cochlear implant system 100 may be configured to perform and/or facilitate various operations involved in fitting the cochlear implant system itself to a recipient (e.g., by detecting and/or analyzing cortical potentials of the recipient, determining or facilitating the determination of fitting parameters, and so forth).

While cochlear implant systems such as cochlear implant system 100 will be described in detail as the focus of this disclosure, it will be understood that other types of hearing systems and medical systems may also implement the principles described herein (e.g., taking the place of the cochlear implant system or operating in concert with the cochlear implant system) in certain instances. As one example, hearing aids that do not include an electrode lead configured for implantation into the recipient may be employed in certain implementations (e.g., either for both ears or in one ear of a bimodal system that also includes a cochlear implant system). In other examples, medical systems that are not necessarily associated with improving the recipient's hearing may also employ principles described herein. For instance, systems and methods described herein may be implemented as part of a spinal cord stimulation system, a visual prosthetic system, or any other implantable prosthetic or other medical system as may serve a particular implementation.

As shown in FIG. 1, cochlear implant system 100 includes a cochlear implant 102, an electrode lead 104 physically coupled to cochlear implant 102 and having an array of electrodes 106, and a processing unit 108 configured to be communicatively coupled to cochlear implant 102 by way of a communication link 110.

The cochlear implant system 100 shown in FIG. 1 is unilateral (i.e., associated with only one ear of the recipient). Alternatively, a bilateral configuration of cochlear implant system 100 may include separate cochlear implants and electrode leads for each ear of the recipient. In the bilateral configuration, processing unit 108 may be implemented by a single processing unit configured to interface with both cochlear implants or by two separate processing units each configured to interface with a different one of the cochlear implants.

Cochlear implant 102 may be implemented by any suitable type of implantable stimulator. For example, cochlear implant 102 may be implemented by an implantable cochlear stimulator. Additionally or alternatively, cochlear implant 102 may be implemented by a brainstem implant and/or any other type of device that may be implanted within the recipient and configured to apply electrical stimulation to one or more stimulation sites located along an auditory pathway of the recipient.

In some examples, cochlear implant 102 may be configured to generate electrical stimulation representative of an audio signal processed by processing unit 108 in accordance with one or more stimulation parameters transmitted to cochlear implant 102 by processing unit 108. Cochlear implant 102 may be further configured to apply the electrical stimulation to one or more stimulation sites (e.g., one or more intracochlear locations) within the recipient by way of one or more electrodes 106 on electrode lead 104. In some examples, cochlear implant 102 may include a plurality of independent current sources each associated with a channel defined by one or more of electrodes 106. In this manner, different stimulation current levels may be applied to multiple stimulation sites simultaneously by way of multiple electrodes 106.

Cochlear implant 102 may additionally or alternatively be configured to generate, store, and/or transmit data. For example, cochlear implant 102 may use one or more electrodes 106 to record one or more signals (e.g., one or more voltages, impedances, evoked responses within the recipient, and/or other measurements) and transmit, by way of communication link 110, data representative of the one or more signals to processing unit 108. In some examples, this data is referred to as back telemetry data.

Electrode lead 104 may be implemented in any suitable manner. For example, a distal portion of electrode lead 104 may be pre-curved such that electrode lead 104 conforms with the helical shape of the cochlea after being implanted. Electrode lead 104 may alternatively be naturally straight or of any other suitable configuration.

In some examples, electrode lead 104 includes a plurality of wires (e.g., within an outer sheath) that conductively couple electrodes 106 to one or more current sources within cochlear implant 102. For example, if there are N electrodes 106 on electrode lead 104 and n current sources within cochlear implant 102, there may be N separate wires within electrode lead 104 that are configured to conductively connect each electrode 106 to a different one of the N current sources. It will be understood that, as used herein, "N" may be used as a placeholder value (e.g., an integer 1 or greater) to generically relate the number of various different types of items described herein. As such, an N used to describe the number of one type of item herein may be different than an N used to describe the number of another item herein. In this case, the number N of electrodes may be 8, 12, 16, or any other suitable number.

Electrodes 106 are located on at least a distal portion of electrode lead 104. In this configuration, after the distal portion of electrode lead 104 is inserted into the cochlea, electrical stimulation may be applied by way of one or more of electrodes 106 to one or more intracochlear locations. One or more other electrodes (e.g., including a ground electrode, not explicitly shown) may also be disposed on other parts of electrode lead 104 (e.g., on a proximal portion of electrode lead 104) to, for example, provide a current return path for stimulation current applied by electrodes 106 and to remain external to the cochlea after the distal portion of electrode lead 104 is inserted into the cochlea. Additionally or alternatively, a housing of cochlear implant 102 may serve as a ground for stimulation current applied by electrodes 106.

Processing unit 108 may be configured to interface with (e.g., control and/or receive data from) cochlear implant 102. For example, processing unit 108 may transmit commands (e.g., stimulation parameters and/or other types of operating parameters in the form of data words included in a forward telemetry sequence) to cochlear implant 102 by way of communication link 110. Processing unit 108 may additionally or alternatively provide operating power to cochlear implant 102 by transmitting one or more power signals to cochlear implant 102 by way of communication link 110. Processing unit 108 may additionally or alternatively receive data (e.g., in a backward telemetry sequence) from cochlear implant 102 by way of communication link 110. Communication link 110 may be implemented by any suitable number of wired and/or wireless bidirectional and/or unidirectional links.

As shown, processing unit 108 includes a memory 112 and a processor 114 configured to be selectively and communicatively coupled to one another. In some examples, memory 112 and processor 114 may be distributed between multiple devices and/or multiple locations as may serve a particular implementation.

Memory 112 may be implemented by any suitable non-transitory computer-readable (e.g., processor-readable) medium such as any combination of non-volatile storage media and/or volatile storage media. Examples of non-volatile storage media may include read-only memory, flash memory, a solid-state drive, a magnetic storage device (e.g., a hard drive), ferroelectric random-access memory ("RAM"), an optical disc, and so forth. Examples of volatile storage media may include RAM (e.g., dynamic RAM) or other types of volatile memory.

Memory 112 may maintain (e.g., store) executable data used by processor 114 to perform one or more of the operations described herein. For example, memory 112 may store instructions 116 that may be executed by processor 114 to perform any of the operations described herein. Instructions 116 may be implemented by any suitable application, program (e.g., sound processing program), software, script, code, and/or other executable data instance. Memory 112 may also maintain any data received, generated, managed, used, and/or transmitted by processor 114.

Processor 114 may be configured to perform (e.g., execute instructions 116 stored in memory 112 to perform) various operations with respect to cochlear implant 102. For instance, processor 114 may perform any of the operations described herein as being performed by processing unit 108, including directing operations performed by cochlear implant 102. As one illustrative operation, processor 114 may receive an audio signal (e.g., by way of a microphone communicatively coupled to processing unit 108, a wireless interface (e.g., a Bluetooth interface), and/or a wired interface (e.g., an auxiliary input port)). Processor 114 may process the audio signal in accordance with a sound processing program (e.g., a sound processing program stored in memory 112) to generate appropriate stimulation parameters. Processor 114 may then transmit the stimulation parameters to cochlear implant 102 to direct cochlear implant 102 to apply electrical stimulation representative of the audio signal to the recipient.

In some implementations, processor 114 may also be configured to apply acoustic stimulation to the recipient. For example, cochlear implant system 100 may be implemented as an electroacoustic hearing system that includes, together with electrode lead 104 for applying electrical stimulation to the recipient, a loudspeaker (also referred to as a receiver) that is optionally coupled to processing unit 108 for delivering acoustic stimulation to the recipient. The acoustic stimulation may be representative of an audio signal (e.g., an amplified version of the audio signal), and may be configured to produce sound at frequencies that the recipient retains an ability to hear and, in certain examples as will be described in more detail below, to produce acoustic stimulation that may elicit an evoked response (e.g., a cortical potential) within the recipient.

Processor 114 may be additionally or alternatively configured to receive and process data generated by cochlear implant 102. For example, processor 114 may receive data representative of a signal recorded by cochlear implant 102 using one or more electrodes 106 and, based on the data, adjust one or more operating parameters of processing unit 108. Additionally or alternatively, processor 114 may use the data to perform one or more diagnostic operations with respect to cochlear implant 102 and/or the recipient.

Other operations may be performed by processor 114 as may serve a particular implementation. In the description provided herein, any references to operations performed by processing unit 108 and/or any implementation thereof may be understood to be performed by processor 114 based on instructions 116 stored in memory 112.

Figure 2:
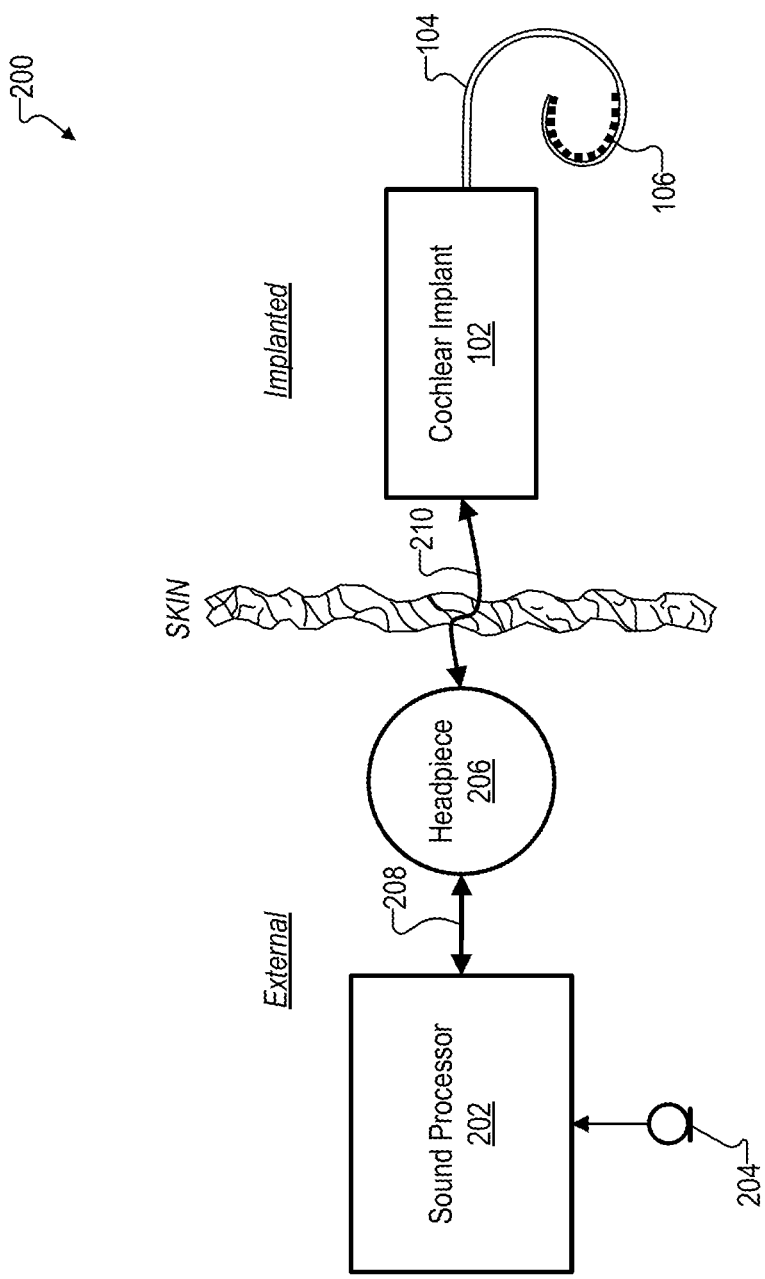
FIGS. 2-3 show illustrative implementations of the cochlear implant system of FIG. 1.

Processing unit 108 may be implemented by one or more devices configured to interface with cochlear implant 102. To illustrate, FIG. 2 shows an illustrative implementation 200 of cochlear implant system 100 in which processing unit 108 is implemented by a sound processor 202 configured to be located external to the recipient. In configuration 200, sound processor 202 is communicatively coupled to a microphone 204 and to a headpiece 206 that are both configured to be located external to the recipient.

Sound processor 202 may be implemented by any suitable device that may be worn or carried by the recipient. For example, sound processor 202 may be implemented by a behind-the-ear ("BTE") unit configured to be worn behind and/or on top of an ear of the recipient. As another example, sound processor 202 may be implemented by an off-the-ear unit (also referred to as a body worn device) configured to be worn or carried by the recipient away from the ear. In yet another example, at least a portion of sound processor 202 may be implemented by circuitry implemented within headpiece 206.

Microphone 204 is configured to detect one or more audio signals (e.g., signals including speech and/or any other type of sound) in an environment of the recipient. Microphone 204 may be implemented in any suitable manner. For example, microphone 204 may be implemented by a microphone that is configured to be placed within the concha of the ear near the entrance to the ear canal, such as a T-MIC™ microphone from Advanced Bionics. Such a microphone may be held within the concha of the ear near the entrance of the ear canal during normal operation by a boom or stalk that is attached to an ear hook configured to be selectively attached to sound processor 202. Additionally or alternatively, microphone 204 may be implemented by one or more microphones in or on headpiece 206, one or more microphones in or on a housing of sound processor 202, one or more beam-forming microphones, and/or any other suitable microphone or set of microphones as may serve a particular implementation.

Headpiece 206 may be selectively and communicatively coupled to sound processor 202 by way of a communication link 208, which may be implemented by a cable or any other suitable wired or wireless communication link as may serve a particular implementation. Headpiece 206 may include an external antenna (e.g., a coil and/or one or more wireless communication components) configured to facilitate selective wireless coupling of sound processor 202 to cochlear implant 102. Headpiece 206 may additionally or alternatively be used to selectively and wirelessly couple any other external device to cochlear implant 102. To this end, headpiece 206 may be configured to be affixed to the recipient's head and positioned such that the external antenna housed within headpiece 206 is communicatively coupled (e.g., by way of an inductive link) to a corresponding implantable antenna such as an implanted coil (and/or one or more other wireless communication components) associated with cochlear implant 102. In this manner, stimulation parameters and/or power signals may be wirelessly and transcutaneously transmitted between sound processor 202 and cochlear implant 102 by way of a wireless and transcutaneous communication link 210.

In configuration 200, sound processor 202 may receive an audio signal detected by microphone 204 by receiving a signal (e.g., an electrical signal) representative of the audio signal from microphone 204. Sound processor 202 may additionally or alternatively receive the audio signal by way of any other suitable interface as described herein. Sound processor 202 may process the audio signal in any of the ways described herein and transmit, by way of headpiece 206, stimulation parameters to cochlear implant 102 to direct cochlear implant 102 to apply electrical stimulation representative of the audio signal to the recipient.

In an alternative configuration, sound processor 202 may be implanted within the recipient instead of being located external to the recipient. In this alternative configuration, which may be referred to as a fully implantable configuration of cochlear implant system 100, sound processor 202 and cochlear implant 102 may be combined into a single device or implemented as separate devices configured to communicate one with another by way of a wired and/or wireless communication link. In a fully implantable implementation of cochlear implant system 100, headpiece 206 may not be included and microphone 204 may be implemented by one or more microphones implanted within the recipient, located within an ear canal of the recipient, and/or located external to the recipient.

Figure 3:
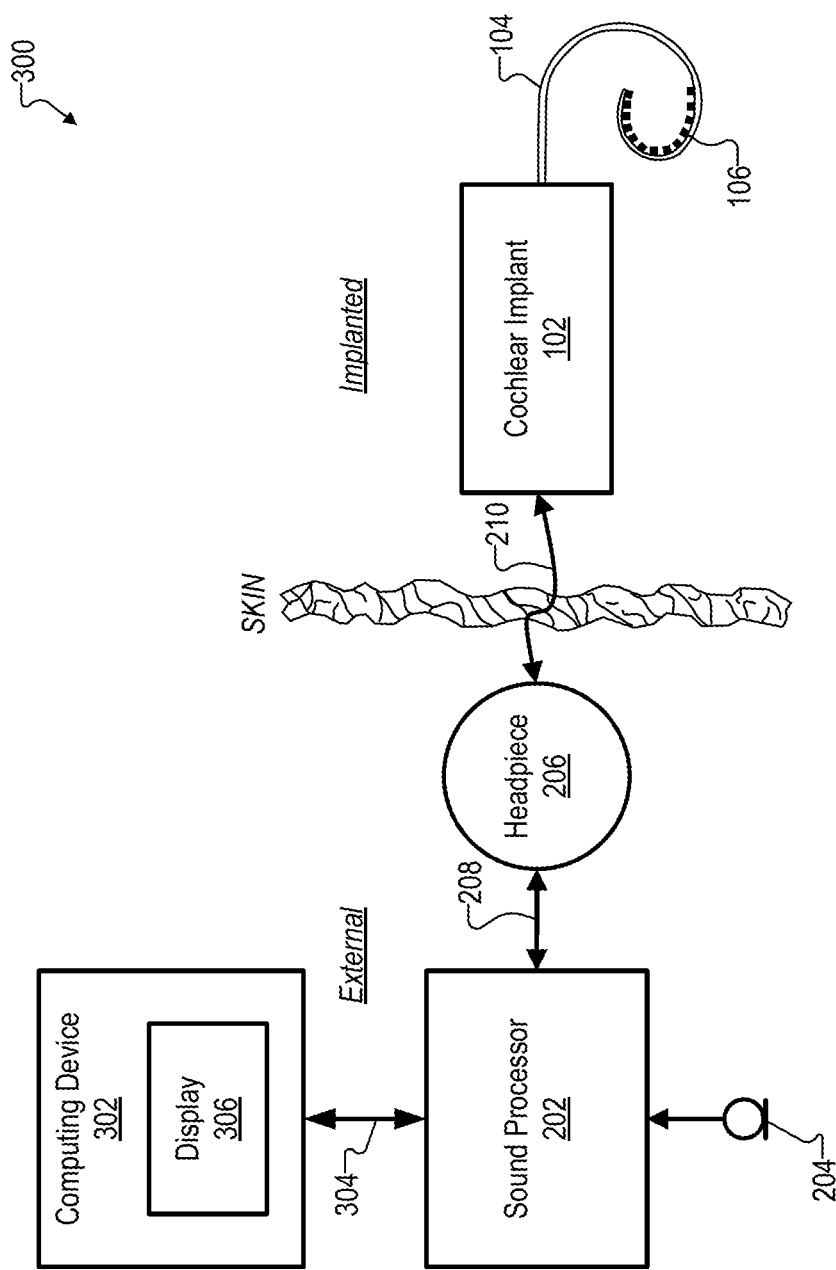

FIG. 3 shows an illustrative implementation 300 of cochlear implant system 100 in which processing unit 108 is implemented by a combination of sound processor 202 and a computing device 302 configured to communicatively couple to sound processor 202 by way of a communication link 304, which may be implemented by any suitable wired or wireless communication link.

Computing device 302 may be implemented by any suitable combination of hardware and software. To illustrate, computing device 302 may be implemented by a mobile device (e.g., a mobile phone, a laptop, a tablet computer, etc.), a desktop computer, a clinical tool configured to facilitate fitting the cochlear implant system to the recipient, and/or any other suitable computing device as may serve a particular implementation. As an example, computing device 302 may be implemented by a mobile device configured to execute an application (e.g., a "mobile app") that may be used by a user (e.g., the recipient, a clinician, and/or any other user). In some instances, such applications may be configured to control one or more settings of sound processor 202 and/or cochlear implant 102 and/or to perform one or more operations (e.g., diagnostic operations, fitting operations, etc.) with respect to data generated by sound processor 202 and/or cochlear implant 102.

In some examples, computing device 302 may be configured to control an operation of cochlear implant 102 by transmitting one or more commands to cochlear implant 102 by way of sound processor 202. Likewise, computing device 302 may be configured to receive data generated by cochlear implant 102 by way of sound processor 202. Alternatively, computing device 302 may interface with (e.g., control and/or receive data from) cochlear implant 102 directly by way of a wireless communication link between computing device 302 and cochlear implant 102. In some implementations in which computing device 302 interfaces directly with cochlear implant 102, sound processor 202 may or may not be included in cochlear implant system 100.

Computing device 302 is shown as having an integrated display 306. Display 306 may be implemented by a display screen or touchscreen, for example, and may be configured to display content generated by computing device 302. Additionally or alternatively, computing device 302 may be communicatively coupled to an external display device (not shown) configured to display the content generated by computing device 302.

In some examples, computing device 302 represents a fitting device configured to be selectively used (e.g., by a clinician) to fit sound processor 202 and/or cochlear implant 102 to the recipient. In these examples, computing device 302 may be configured to execute a fitting program configured to determine and set one or more operating parameters of sound processor 202 and/or cochlear implant 102 to values that are optimized for the recipient. As such, in these examples, computing device 302 may not be considered to be part of cochlear implant system 100. Instead, computing device 302 may be considered to be separate from cochlear implant system 100 such that computing device 302 may be selectively coupled to cochlear implant system 100 when it is desired to fit sound processor 202 and/or cochlear implant 102 to the recipient.

As one example of functionality that cochlear implant system 100 or a fitting system associated therewith (e.g., a fitting system separate from cochlear implant system 100 such as by being implemented by a computing device 302 in the manner described above) may perform, FIG. 4 shows an illustrative method 400. Method 400 may serve as an illustrative method for fitting a hearing system to a recipient based on cortical potentials of the recipient. Method 400 may be performed by any configuration or implementation of cochlear implant system 100 described herein or by another suitable hearing system or medical system as may serve a particular implementation. For instance, method 400 may be performed by an implementation of cochlear implant system 100 such as implementation 200 of FIG. 2 or implementation 300 of FIG. 3. In other examples, method 400 may be performed by a fitting system separate from the hearing system, or by another type of hearing system or non-hearing medical system as may serve a particular implementation (e.g., an electroacoustic hearing system, a hearing aid system, a bimodal system, etc.).

Figure 4:
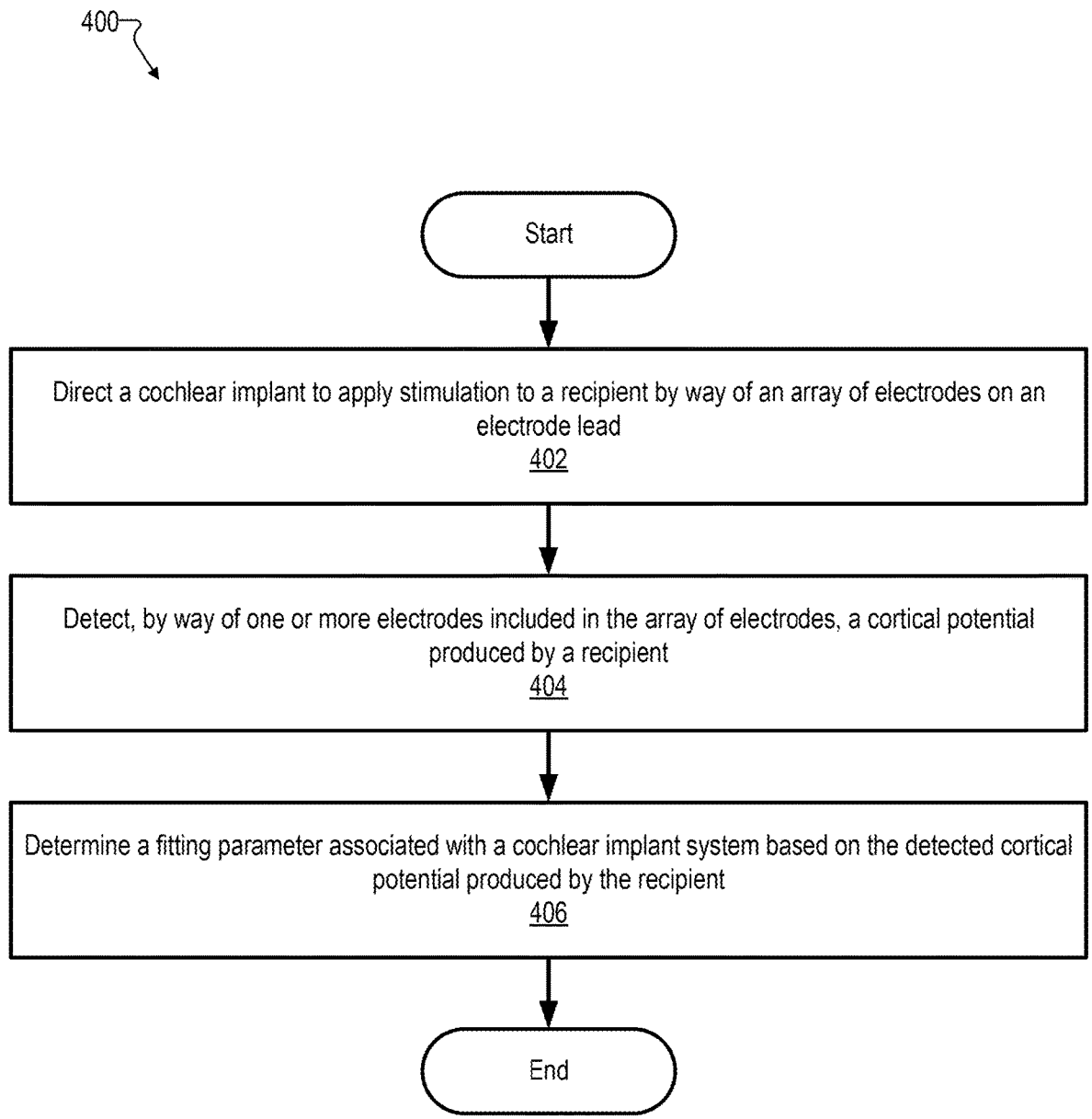
FIG. 4 shows an illustrative method for fitting a hearing system such as the cochlear implant system of FIG. 1 to a recipient based on cortical potentials of the recipient.

While FIG. 4 shows illustrative operations according to one embodiment, other embodiments may omit, add to, reorder, and/or modify any of the operations shown in FIG. 4. In some examples, multiple operations shown in FIG. 4 or described in relation to FIG. 4 may be performed concurrently (e.g., in parallel) with one another, rather than being performed sequentially as illustrated and/or described.

In some examples, the operations of FIG. 4 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Each of operations 402-406 of method 400 will now be described in more detail as the operations may be performed by cochlear implant system 100 (e.g., by processing unit 108), an implementation thereof, or another suitable hearing system, medical system, or dedicated fitting system.

At operation 402, cochlear implant system 100 may direct the cochlear implant to apply stimulation to the recipient by way of the array of electrodes 106 of electrode lead 104. This stimulation may be provided in any of the ways described above in relation to FIGS. 1-3, such as by using any suitable sound processing programs, by basing the stimulation on any suitable audio source (e.g., microphone 204, an audio input signal provided by computing device 302, etc.), and so forth. The stimulation provided at operation 402 by way of electrodes 106 may be electrical stimulation that is applied to the cochlea in a tonotopic manner in which stimulation associated with different frequencies is applied at different parts of the recipient's cochlea that correspond to the different frequencies. In some examples, electrical stimulation provided at operation 402 may be provided together with acoustic stimulation provided by way of a loudspeaker (e.g., such as for one of the electroacoustic hearing system implementations of cochlear implant system 100 mentioned above).

As will be described in more detail below, the stimulation that the cochlear implant is directed to apply at operation 402 may, in certain examples, serve as stimulation configured to evoke responses (e.g., evoked cortical potentials, etc.) from the recipient. In other examples, stimulation aimed at evoking a response from the recipient may not be employed or may be separate from electrical stimulation applied as part of operation 402. Regardless of whether or not electrodes 106 of electrode lead 104 are used to apply stimulation to evoke a response, however, it will be understood that one or more of these same electrodes 106 that are used to apply stimulation during normal operation of cochlear implant system 100 may also be employed for detecting certain cortical potentials that are produced by the recipient and used to perform fitting procedures described herein.

At operation 404, cochlear implant system 100 may detect one or more cortical potentials produced by the recipient. As mentioned above, the cortical potentials detected at operation 404 may be detected by way of one or more electrodes included in the array of electrodes 106 of cochlear implant system 100 (i.e., one or more electrodes from the same array of electrodes 106 used to provide stimulation to the recipient at operation 402). In certain examples, along with or instead of being detected by way of the one or more electrodes 106 of cochlear implant system 100, one or more cortical potentials and/or other evoked or non-evoked responses (e.g., the cortical potentials of operation 404) may also be detected using electrodes or other sensors other than the electrodes 106. For instance, external electrodes placed on the head of the recipient, implanted electrodes dedicated to cortical potential monitoring, and/or other such electrodes may be employed in certain implementations.

In certain examples, cochlear implant system 100 may perform operation 404 automatically and/or in an automated way (e.g., without necessarily being initiated and/or overseen by a human being such as a clinician). In other examples, however, a human user (e.g., a clinician responsible for performing a fitting procedure with respect to cochlear implant system 100, the recipient, a caretaker of the recipient, etc.) may be involved in directing the performance of operation 404. For instance, the detecting of the cortical potential at operation 404 may be performed in these examples under direction of the user such as by being initiated by the user, by being performed based on input from the user, by using electrodes or other sensors put in place or initialized by the user, or the like. In certain examples, the user may perform any of these or other tasks based on instruction provided by cochlear implant system 100 or a fitting system associated therewith (e.g., user instructions presented by computing device 302 by way of display 306, etc.).

The detecting of the one or more cortical potentials at operation 404 may be performed under any of various suitable circumstances. For example, in certain implementations, a fitting procedure may be configured to employ cortical potentials such that operation 404 may be an integral part of the fitting procedure whenever the procedure is performed. While behavioral and other fitting methodologies (e.g., ECochG tests, neural response imaging ("NRI"), electrically evoked compound action potentials ("ECAPs"), etc.) may sometimes be available and well suited for facilitating and optimizing fitting procedures involving hearing systems that rely only on electrical stimulation, fitting procedures for hearing systems used by recipients retaining at least some residual hearing (e.g., electroacoustic hearing systems, bimodal hearing systems, etc.) may benefit from acoustically evoked responses such as may be represented by cortical potentials detected using electroencephalogram ("EEG") tests or the like. In certain of these examples, cortical potentials alone may be measured, while, in other examples, a combination of cortical potentials and electrically evoked potentials (e.g., ECochG) may be used to fit an electroacoustic or bimodal system to a recipient.

Rather than being included as an integral part of the fitting procedure, cortical potentials may, in certain implementations, be detected and employed only when other modes of detecting hearing characteristics and preferences of the recipient are unavailable. For instance, certain fitting procedures may use behavioral responses provided by the recipient (i.e., verbal or other voluntary input expressed by the recipient to indicate, for instance, whether test sounds are a comfortable level, are uncomfortably loud, are just short of being uncomfortably loud, are just loud enough to be perceptible, etc.). Even in situations where behavioral responses are not available (e.g., because the recipient is unable to provide such information due to age, disability, etc.), electrically evoked responses such as ECochG, NRI, ECAP, or other responses may be available and used as a primary input to facilitate the fitting procedures. However, if behavioral and/or ECochG or other types of response methodologies are unavailable or insufficient to facilitate a particular fitting procedure under a particular set of circumstances, acoustically evoked cortical potentials (or other cortical potentials such as electrically-evoked or non-evoked potentials) may be employed.

Specifically, for instance, certain implementations of cochlear implant system 100 may be configured to determine, prior to or as part of operation 404, that a behavioral fitting methodology and an ECochG fitting methodology (such as described above) are both unavailable for determining the fitting parameter. This may be the case due to abilities of the recipient (e.g., an ability or lack of ability to hear acoustically), circumstances surrounding how or when the fitting procedure is to be carried out, the amount or nature of human oversight that may be available for a given fitting procedure, or for various other reasons. The detecting of the one or more cortical potentials at operation 404 (as well as the determining of the fitting parameter based on the detected cortical potentials, as will be described below in relation to operation 406) may then be performed in response to the determining that the behavioral and ECochG fitting methodologies are unavailable for determining the fitting parameter. In other words, in these implementations, cortical-potential-based fitting methodologies may be used as a fallback when other methodologies fail or are unavailable for a variety of reasons.

At operation 406, cochlear implant system 100 may determine one or more fitting parameters based on one or more cortical potentials detected at operation 404. For example, the fitting parameters may be associated with cochlear implant system 100 by defining characteristics of the cochlear implant system, how the cochlear implant system is to operate with respect to the recipient, or the like. The fitting parameters determined at operation 406 may be customized to (e.g., unique to, specific to, etc.) the cochlear implant system 100 itself, and/or to the particular recipient who is to use the cochlear implant system and who produced the cortical potentials upon which the fitting parameters are based. To this end, the fitting parameters may include any of the types of fitting parameters described herein and may be determined based on cortical potentials or other recipient input in any manner as may serve a particular implementation. For example, various stimulation parameters that may be determined during a fitting procedure include, but are not limited to, an M-level value representative of a most comfortable sound level for the recipient, a T-level value associated with a softest sound that the recipient is capable of hearing, an loudness threshold at which sounds become uncomfortably loud to the user, various gains or other operating parameters for the cochlear implant system, and other fitting parameters that will be described or may serve a particular implementation.

Figure 5:
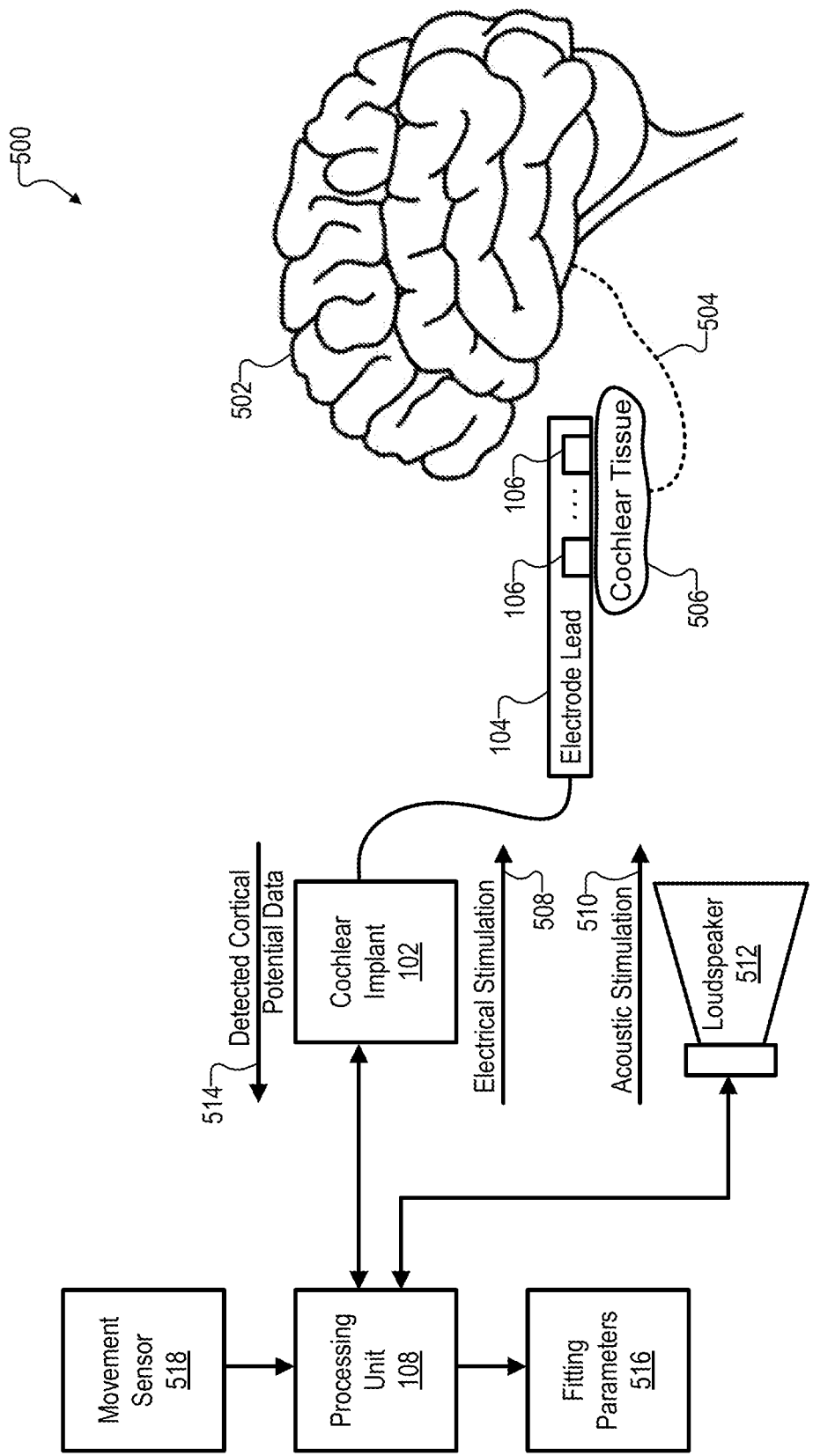
FIG. 5 shows an illustrative configuration in which components of the cochlear implant system of FIG. 1 operate to fit a hearing system to a recipient based on cortical potentials of the recipient.

FIG. 5 shows an illustrative configuration 500 in which certain components of cochlear implant system 100 operate to fit the cochlear implant system to a recipient based on cortical potentials of the recipient in accordance with principles described herein. As shown in FIG. 5, a brain 502 of a recipient may produce cortical potentials 504 that may be detected by electrodes 106 (e.g., a detecting electrode and a ground electrode) of electrode lead 104 as the electrodes detect electrical signals in cochlear tissue 506 where the electrodes are disposed.

In some examples, cortical potentials 504 may be evoked potentials that are emitted in response to different types of stimulation. For instance, FIG. 5 shows electrical stimulation 508 that may be applied by cochlear implant 102 (e.g., by directing the stimulation to be applied to cochlear tissue 506 by electrodes 106 of electrode lead 104) to evoke a cortical potential response. As another example, FIG. 5 also shows acoustic stimulation 510 that may be applied by a loudspeaker 512 (e.g., a loudspeaker included within an electroacoustic hearing system, a bimodal hearing system with a hearing aid, etc.). Whichever type of stimulation may be applied in a particular implementation (e.g., electrical stimulation 508 or acoustic stimulation 510) the stimulation may be directed by processing unit 108, which may have some degree of control over cochlear implant 102 and/or loudspeaker 512. Additionally, back telemetry from cochlear implant 102 may be provided to processing unit 108 to transmit data that has been detected using electrodes 106 of electrode lead 104. For example, as shown, cortical potential data 514 representative of cortical potentials 504 that have been detected by electrodes 106 may be transmitted by cochlear implant 102 to processing unit 108.

Processing unit 108 may be configured not only to direct stimulation to be applied to the recipient (as has been described), but may also receive and process cortical potential data 514 that is received from cochlear implant 102. For example, processing unit 108 may use cortical potential data 514 to determine one or more fitting parameters 516 associated with fitting cochlear implant system 100 to the recipient. In some examples, the processing of cortical potential data 514 to determine fitting parameters 516 may be performed in a manner that accounts for movements of the recipient that may affect cortical potentials 504 or the detection thereof. Such movements may be detected by a movement sensor 518, which may provide data representative of the movements of the recipient to processing unit 108.

Various additional details of the components illustrated in configuration 500, as well as aspects of a fitting procedure that is performed using configuration 100 to fit cochlear implant system 100 to the recipient, will now be described in relation to FIGS. 6-9 with further reference to FIG. 5.

Brain 502 of the recipient of cochlear implant system 100 may constantly produce cortical potentials and/or other voltage fluctuations and brain waves. As used herein, a cortical potential (also known as a central potential, an auditory potential, a brain wave potential, etc.) may refer to any type of voltage fluctuation emitted by the brain (e.g., the cerebral cortex, the midbrain, the brainstem, other portions of the auditory pathway, etc.) that is detectable by way of an EEG test or another such brain wave measurement tool. For instance, processing unit 108 may be configured to perform an EEG test using one or more electrodes 106 included in the array of electrodes of electrode lead 104, and the detecting of one or more cortical potentials 504 may be performed as part of the EEG test.

Certain cortical potentials 504 may be produced by normal brain activity without any specific test stimulus being applied to evoke the cortical potential response.

In contrast, other cortical potentials 504 may be emitted as evoked responses (i.e., evoked potentials) to a particular stimulus (e.g., electrical stimulation 508, acoustic stimulation 510, and/or other suitable test stimuli that evoke a reaction by brain 502). For instance, event-related potentials ("ERPs"), auditory steady state responses ("ASSRs"), auditory brainstem responses ("ABRs"), electrical auditory brainstem responses ("EABRs"), mid latency responses (MLR), late latency responses (LLR), and/or other evoked responses may be included among the cortical potentials 504 to indicate evoked or non-evoked activity of brain 502.

Figure 6:
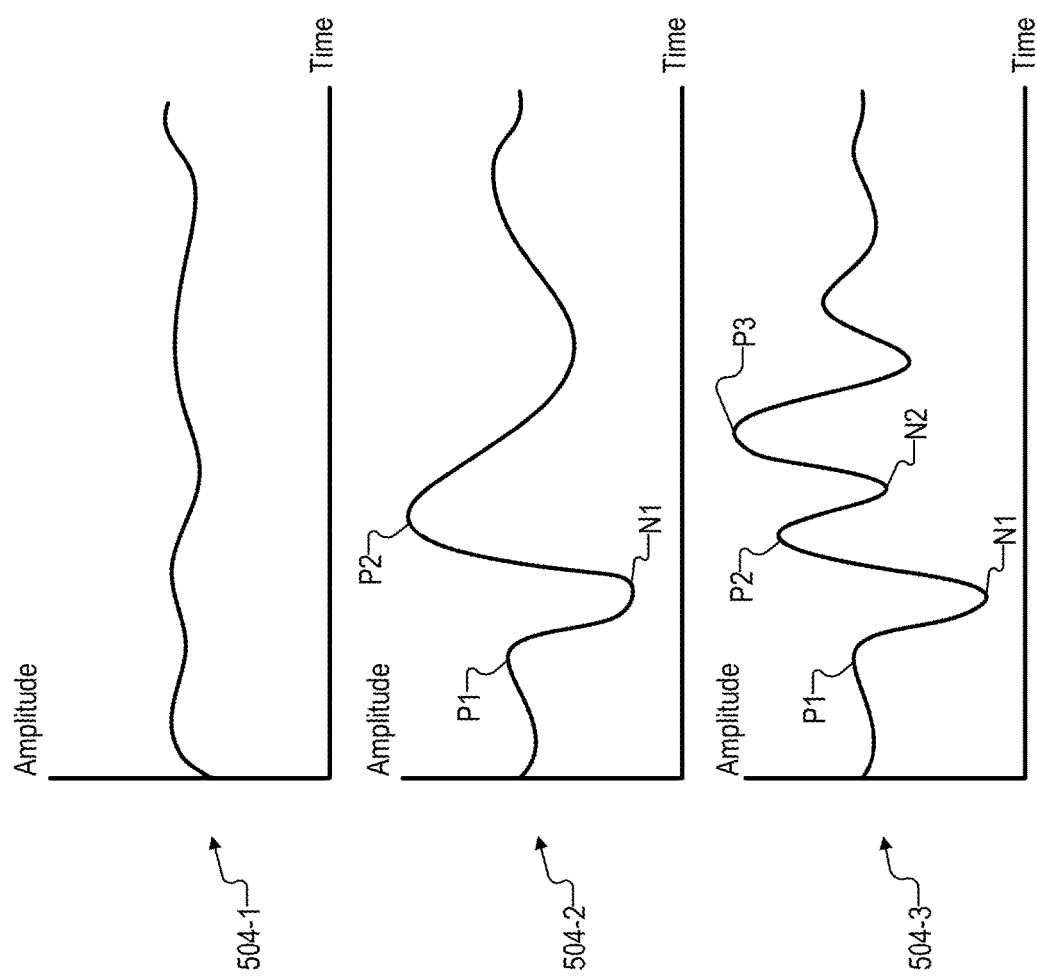
FIG. 6 shows illustrative cortical potentials that may be detected by the configuration of FIG. 5.

FIG. 6 shows examples of illustrative cortical potentials 504 that may be detected using configuration 500 of FIG. 5. Specifically, as shown in FIG. 6, a cortical potential 504-1 shows an example of a non-evoked cortical potential detected when brain 502 is relatively neutral and not responding to any particular stimulus. While certain amplitude peaks may be present in this type of example, it is shown that it may be more difficult for processing unit 108 to derive helpful information from this non-evoked example. In contrast, cortical potentials 504-2 and 504-3 each represent examples of cortical potentials that are evoked in response to certain stimuli applied to the recipient. For instance, the stimulus applied to evoke the example of cortical potential 504-2 is shown to cause brain 502 to produce certain peaks such as a P1, N1, and P2 peak that are each identifiable by processing unit 108 when cortical potential 504-2 is received and analyzed. As another example, the stimulus applied to evoke the example of cortical potential 504-3 is shown to cause brain 502 to produce not only the P1, N1, and P2 peaks, but also to include an N2 and separate P3 peak (also referred to as a P300 peak) that is also identifiable by processing unit 108 when cortical potential 504-3 is received and analyzed.

Certain peaks detected from different cortical potentials 504 may be indicative of what brain 502 of the recipient is experiencing even if the recipient has difficulty in articulating or otherwise behaviorally expressing that experience for various reasons. For example, as will be described in more detail below, the latency of the P1 peak (e.g., how much time separates the P1 peak from the application of the stimulation that evokes the cortical potential) may be indicative of how responsive brain 502 acts under test conditions associated with a particular stimulation. As another example, the P3 (or P300) peak may be evoked from brain 502 when brain 502 is processing a stimulus such as to make a decision based on the stimulus. As a result, the occurrence of the P3 peak may be indicative that the recipient is reacting to a stimulus in a particular manner that goes beyond a physiological reflexive reaction. For example, the presence of the P3 peak in cortical potential 504-3 may signify that something about the stimulation applied in that example (e.g., a change to the stimulation as compared to stimulation applied to evoke cortical potential 504-2, etc.) is consciously identified by the recipient as being differentiable from other stimuli that have been applied (e.g., the stimulus is novel, etc.). Accordingly, the presence or absence of the P3 peak in response to different stimulation configurations may be interpreted to identify certain aspects of how the recipient perceives the stimulation (e.g., whether the recipient can differentiate or discriminate between different stimuli, etc.).

As one example of how the presence or absence of the P3 peak may be useful to objectively analyze the experience of brain 502 without needing to rely on behavioral feedback deliberately provided by the recipient, a first stimulus that evokes cortical potential 504-2 (without a P3 peak) and a second stimulus that evokes cortical potential 504-3 (with a P3 peak) will be considered. In this example, both first and second stimuli could include a same electrical stimulation component while only the second stimulus includes an acoustic stimulation component. Alternatively, each stimulus in this example could include both electrical and acoustic stimulation components, but the acoustic stimulation component may be of greater intensity in the second stimulus than the in the first stimulus.

While cortical potential 504-2 illustrates several expected peaks (e.g., P1, N1, P2, etc.), it may be seen that the first stimulus associated with cortical potential 504-2 has failed to elicit a P3 peak. In contrast, due to the difference between the first stimulus and the second stimulus, FIG. 6 shows that a P3 peak is present in cortical potential 504-3 after the other expected peaks (i.e., after the P1, N1, and P2 peaks).

As processing unit 108 objectively evaluates these differences (e.g., in an effort to determine one or more fitting parameters 516) processing unit 108 may determine, for a given set of fitting parameters 516, whether the recipient is able to differentiate the different stimuli. From this determination, it may be determined whether the recipient has viable acoustic hearing (e.g., residual hearing at certain frequencies, etc.) and/or how sensitive or effective the acoustic hearing of the recipient might be. For example, processing unit 108 may detect the absence of the P3 peak in cortical potential 504-2 and the presence of the P3 peak in cortical potential 504-3 as different stimuli are presented. The stimuli may differ in any suitable way such as mentioned above. For instance, after only electrical stimulation has been applied for one or more EEG tests (resulting in cortical potentials such as cortical potential 504-2), an EEG test may be performed where an acoustic stimulation component is also provided with the electrical stimulation component. If the recipient identifies that the stimulation is different (i.e., because the recipient perceives the acoustic stimulus as being separate from the electrical stimulus), the P3 peak may be detectable within the resultant cortical potential (e.g., such as shown in cortical potential 504-3) and processing unit 108 may conclude that the recipient retains at least some acoustic hearing ability.

When the cortical potential produced by the recipient indicates that the recipient perceives acoustic stimulation that has evoked the cortical potential in this way (e.g., by processing unit 108 identifying the presence of the P3 peak on cortical potential 504-3), processing unit 108 may be configured to provide a recommendation to a user. For instance, based on the detected cortical potential indicating that the recipient perceives the acoustic stimulation, processing unit 108 may make a recommendation to a user (e.g., a clinician, the recipient, etc.) that a hearing system that leverages both electrical and acoustic stimulation (i.e., applies both electrical and acoustic stimulation to the recipient) is to be prescribed for use by the recipient. As one example, a recommendation for an electroacoustic hearing system or a bimodal hearing system with a hearing aid (rather than, for example, a bilateral cochlear implant system or another such hearing system that relies exclusively on electrical stimulation) may be made such that the recipient may benefit from his or her ability to perceive acoustic stimulation.

In contrast, if the recipient fails to identify that the stimulation is different in this testing scenario (i.e., because the recipient cannot sufficiently perceive the acoustic stimulus as being separate from the electrical stimulus), the P3 peak may be absent on each cortical potential (e.g., such that a waveform such as cortical potential 504-3 is never generated) and processing unit 108 may determine that the recipient does not have a useable acoustic hearing ability. In this example, processing unit 108 may make a recommendation to the user that an electric-stimulation-only hearing system (e.g., a bilateral cochlear implant system) is to be prescribed for use by the recipient.

Another example will now be considered to illustrate how the analysis of cortical potentials 504 (and including the identification of the presence and/or absence of P3 peaks on different cortical potentials) may be employed in certain implementations. In this example, the stimulation provided for each test may be the same, and may include a plurality of different stimuli (e.g., two simple or complex tones of different pitches, two vowels, two spectral ripple stimuli which differ in either modulation depth or modulation frequencies, etc.). In these tests, different cochlear implant system programming (e.g., using different test parameters) may be applied for different tests and the presence or absence of the P3 peak may be used to indicate how well the programming for a given test allows the recipient to differentiate between the different components of the stimulus. For example, programming changes may lead to different outcomes for the cortical potentials produced by the recipient, which may indicate the extent to which the programming changes help the recipient discriminate between different stimuli.

The cortical potential produced and detected under these testing circumstances may be used to indicate the extent to which the recipient may retain usable acoustic hearing ability or used for other suitable purposes. For example, processing unit 108 may provide the same stimulus and different programming parameters for each test and may determine which programming parameters are optimal based on the size, latency, or other aspects of the P3 peak detected in the resultant cortical potential. For example, an optimal set of test parameters (e.g., fitting parameters that are optimally fitted to a recipient) may allow the recipient to successfully discriminate between different sounds even when the difference between the sounds is relatively slight. Accordingly, test parameters that lead a recipient to produce strong P3 peaks for relatively minor stimulation differences may be determined to be more optimal fitting parameters than fitting parameters that lead the recipient to produce weak P3 peaks or fail to produce P3 peaks at all.

Returning to FIG. 5, different types of test stimulation (e.g., stimulation 508 and 510) are shown. In certain examples, processing unit 108 may be configured to direct such test stimulation to be applied to the recipient to thereby evoke responses such as cortical potentials 504-2 and 504-3 illustrated in FIG. 6. In such examples where cortical potentials 504 are evoked potentials produced by the recipient (e.g., by brain 502 of the recipient) in response to test stimulation, the test stimulation may be implemented by at least one of: 1) electrical stimulation applied to the recipient by way of the array of electrodes 106 (e.g., the electrodes 106 shown in configuration 500 or one or more other electrodes of electrode lead 104), or 2) acoustic stimulation applied to the recipient by loudspeaker 512 as the loudspeaker is directed by processing unit 108.

Electrical stimulation 508 may be applied by electrode lead 104 in any of the ways and by any of the cochlear implant system 100 implementations that have been described. In contrast, acoustic stimulation 510 may be provided only by hearing system implementations that include or are associated with a loudspeaker 512 that the processing unit 108 is able to direct.

As one example, cochlear implant system 100 may be included within a bimodal hearing system together with a hearing aid system employed contralaterally to cochlear implant system 100 on a different ear of the recipient than cochlear implant system 100. In this example, acoustic test stimulation 510 may be provided by a loudspeaker 512 that is included within the hearing aid system and is configured to provide acoustic stimulation 510 when directed by processing unit 108. For example, the cochlear implant and hearing aid systems included within the bimodal hearing system may be communicatively coupled to one another by way of a wireless link such that the processing unit 108 of the cochlear implant system may direct tests that rely on acoustic stimulation applied by a loudspeaker 512 of the hearing aid system.

As another example, cochlear implant system 100 may be implemented as an electroacoustic hearing system that includes a loudspeaker 512 as part of the electroacoustic hearing system. In this example, the loudspeaker 512 of the electroacoustic hearing system may apply acoustic test stimulation 510 to the recipient as directed by processing unit 108 of the electroacoustic hearing system. In still other examples, a loudspeaker 512 that is not included within the implementation of cochlear implant system 100 may be used for testing purposes and may be controlled by an implementation of processing unit 108 such as a clinical fitting tool, a mobile device, or another type of computing device 302.

Figure 8:
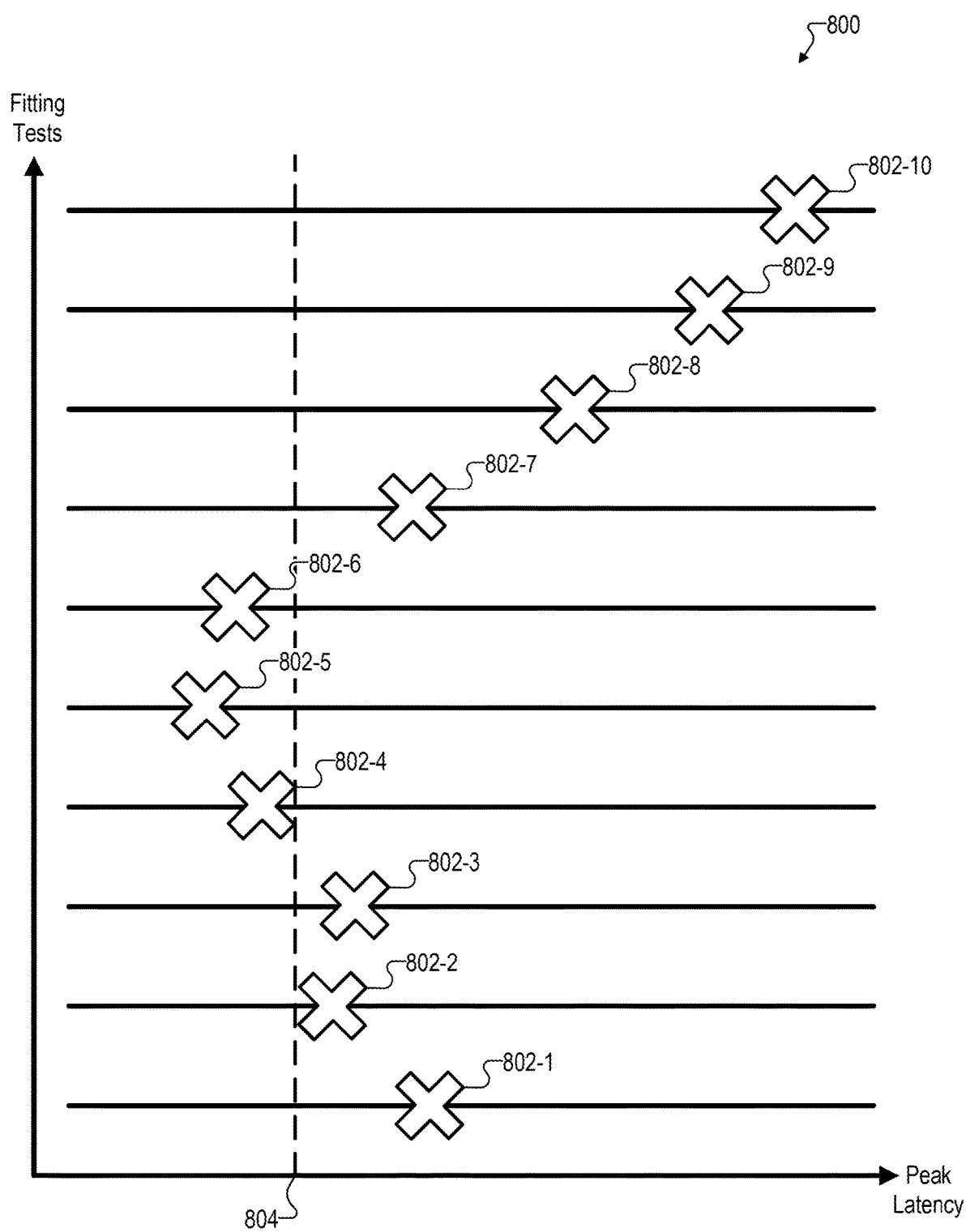
Figure 9:
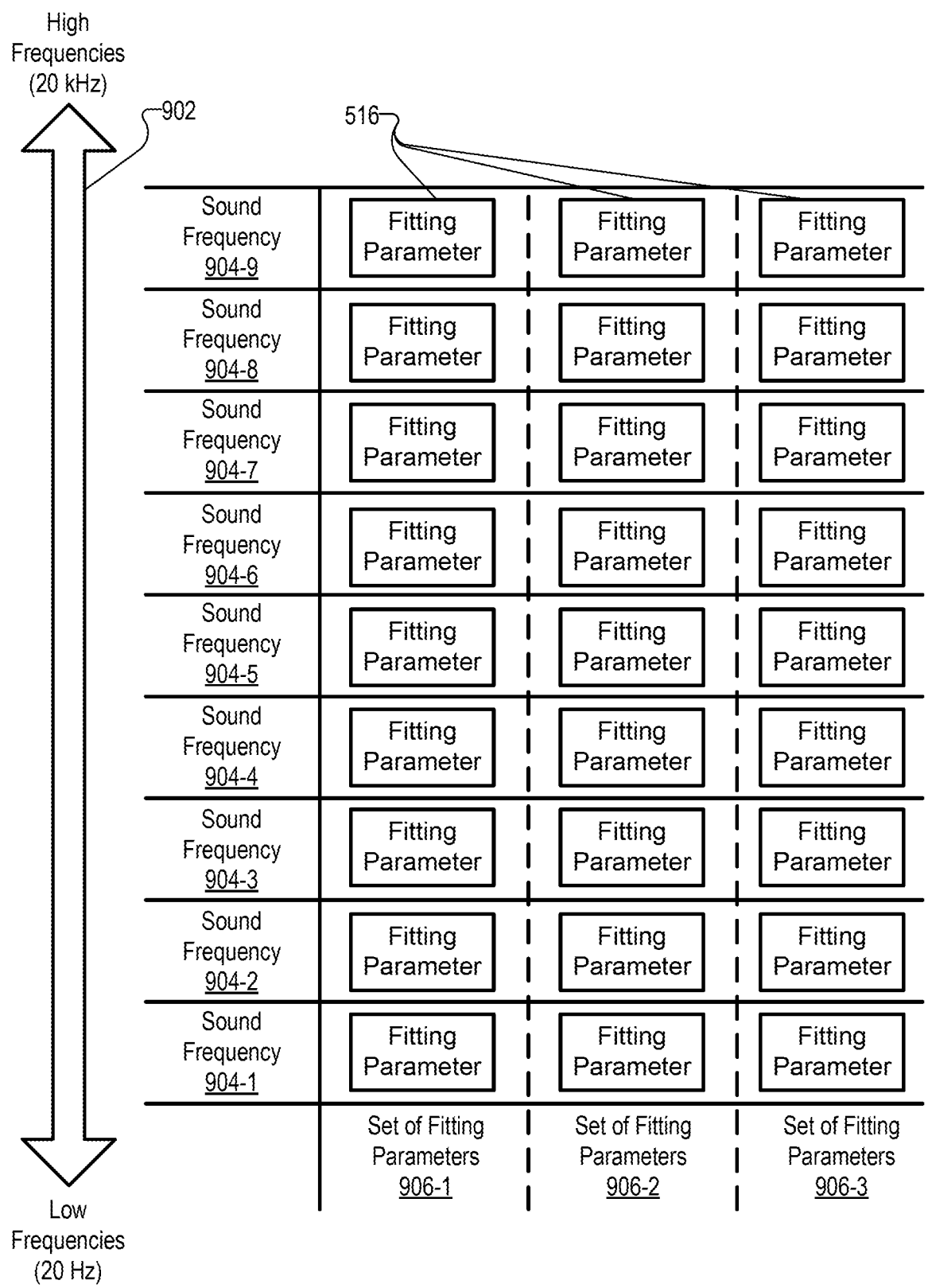

Fitting parameters 516 may be generated by processing unit 108 in any suitable way and may include any fitting parameters as may serve a particular implementation. To illustrate, FIGS. 7-9 show illustrative aspects of how certain fitting parameters may be determined based on detected characteristics of cortical potentials 504 that are detected as part of fitting tests performed on the recipient of cochlear implant system 100 and that are represented by cortical potential data 514 received from cochlear implant 102.

Figure 7:
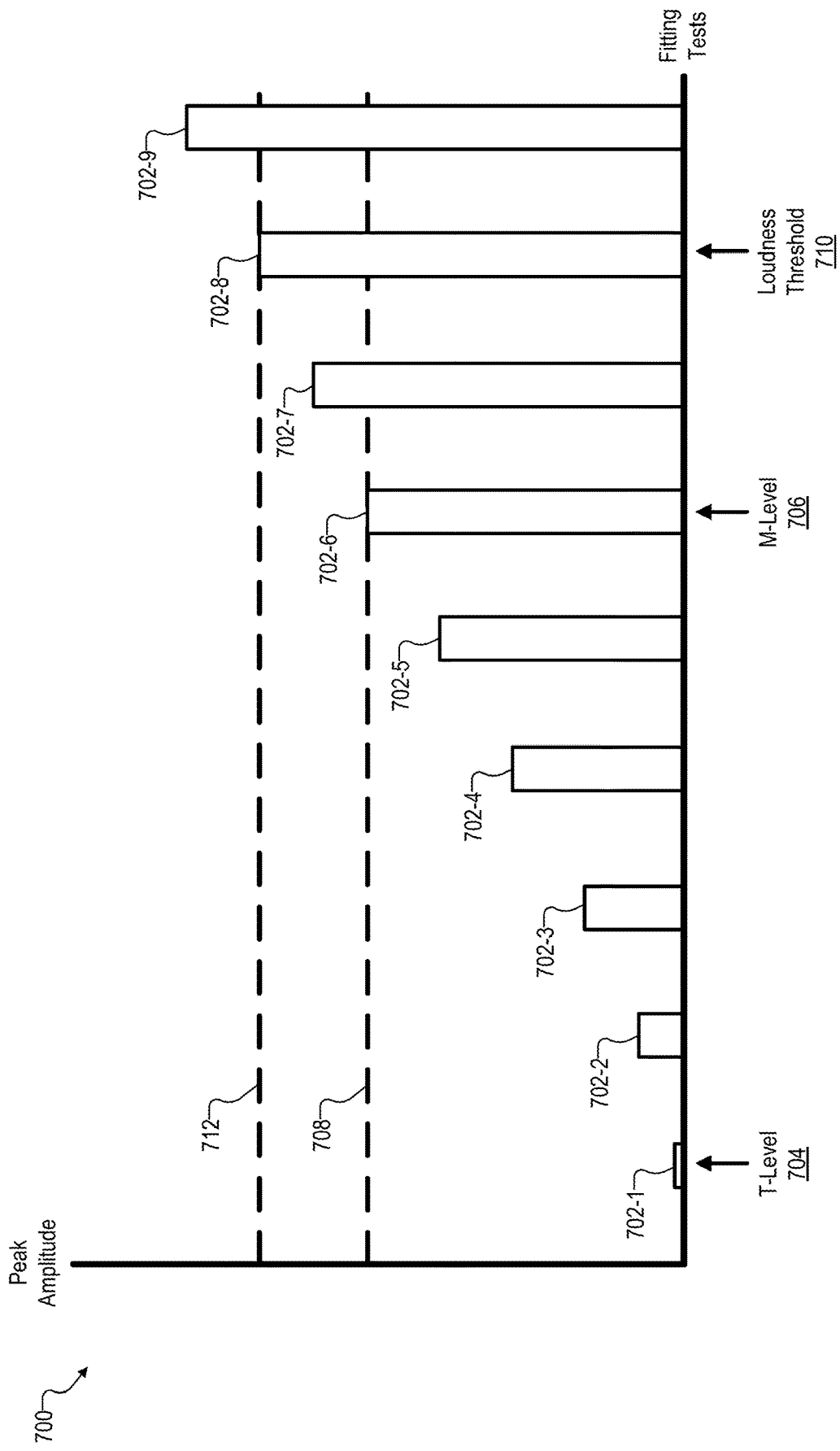
FIGS. 7-9 show illustrative aspects of how certain fitting parameters may be determined based on detected characteristics of cortical potentials that are measured as part of fitting tests performed on a hearing system recipient.

FIG. 7, for example, shows amplitudes of a particular peak (e.g., the P1 peak, etc.) for cortical potentials 504 measured as part of several different fitting tests. More particularly, FIG. 7 shows a graph having a horizontal axis along which different fitting tests are represented and a vertical axis along which is represented a respective peak amplitude value for each particular peak detected as part of each fitting test. For example, a respective amplitude 702 (e.g., one of amplitudes 702-1 through 702-9) may be determined as the amplitude of the P1 peak of each respective cortical potential 504 detected as part of each different fitting test that is performed.

As shown, based on these amplitudes 702, various fitting parameters 516 may be determined. For instance, one fitting parameter may be a T-level 704 that is representative of a softest sound level the recipient is capable of perceiving. T-level 704 may be determined based on the lowest amplitude 702 that is non-zero or that meets a particular threshold level. Any non-zero amplitude 702 (or amplitude that satisfies the particular threshold level) may indicate that brain 502 of the recipient perceived the stimulus, and the smallest of all such amplitudes 702 (i.e., amplitude 702-1 in the example of FIG. 7) may represent the stimulus that is the smallest that the recipient is capable of perceiving. Accordingly, as shown, T-level 704 may correspond to amplitude 702-1 (e.g., may be derived based on the stimulus that was applied to evoke the cortical potential associated with amplitude 702-1).

Another fitting parameter 516 that processing unit 108 may determine based on cortical potential data 514 may be an M-level 706 that is representative of a most comfortable sound level for the recipient. M-level 706 may be determined based on whichever of the amplitudes 702 is nearest to an amplitude level 708 that is associated with the most comfortable sound level for the recipient. For example, it may be expected that a particular peak amplitude level is associated with comfortable and desirable sound levels as perceived by the recipient, and this particular level may be used as amplitude level 708. Whichever of the fitting tests evokes a cortical potential having an amplitude 702 closest to this ideal level (i.e., the fitting test associated with amplitude 702-6 in this example) may be used to derive M-level 706. Accordingly, as shown, M-level 706 may correspond to amplitude 702-6 (e.g., may be derived based on the stimulus that was applied to evoke the cortical potential associated with amplitude 702-6).

Yet another fitting parameter 516 that processing unit 108 may determine based on cortical potential data 514 may be a loudness threshold 710 that is representative of an upper comfort level at which the recipient perceives sound as uncomfortably loud. Loudness threshold 710 may be determined based on whichever of the amplitudes 702 is nearest to, but less than, an amplitude level 712 that is associated with the sound level at which the recipient is likely to perceive pain, receive hearing damage, or otherwise subjectively find the sound to be too loud. For example, it may be expected that a particular peak amplitude level is associated with sound levels that are just loud enough to be uncomfortable, harmful, or otherwise undesirable for the recipient, and this particular level may be used as amplitude level 712. Whichever of the fitting tests evokes a cortical potential having an amplitude 702 closest to, but less than, this upper level (i.e., the fitting test associated with amplitude 702-8 in this example) may be used to derive loudness threshold 710. Accordingly, as shown, loudness threshold 710 may correspond to amplitude 702-8 (e.g., may be derived based on the stimulus that was applied to evoke the cortical potential associated with amplitude 702-8).

In still other examples, other fitting parameters 516 may be determined by processing unit 108 based on cortical potential data 514. For instance, parameters associated with optimizing the bandwidth and/or gain of acoustic stimulation being provided may be determined based on peak amplitudes detected for different fitting tests in any manner as may serve a particular implementation. As another example, parameters determined to help optimize power consumption or other characteristics of cochlear implant system 100 for the recipient may be determined.

Along with determining fitting parameters 516 based on differences in peak amplitudes 702 that may be detected in different fitting tests, processing unit 108 may also determine certain fitting parameters 516 based on other characteristics that may be detected in different fitting tests. For example, FIG. 8 shows latencies of a particular peak (e.g., the P1 peak, the P3 peak, etc.) for cortical potentials 504 as part of the same or other fitting tests as represented in FIG. 7. More particularly, FIG. 8 shows a graph having a vertical axis along which different fitting tests are represented and a horizontal axis along which is represented a respective peak latency time for each particular peak detected as part of each fitting test. For example, a respective latency 802 (e.g., one of latencies 802-1 through 802-10) may be determined as the latency of the relevant peak (e.g., the P1 peak, the P3 peak, etc.) of each respective cortical potential 504 detected as part of each different fitting test that is performed.

As shown, based on these latencies 802, various fitting parameters 516 may be determined. For instance, the latency at which cortical responses are received for different fitting tests may be used as an indicator of which programming configuration (e.g., which fitting parameters, etc.) will be most optimal for the recipient. Specifically, the time it takes for the brain to react to a particular acoustic stimulus, which is measured as the latency at which a particular cortical potential peak is detected, may be indicative of the quality level the brain perceived for the test stimulation. In other words, for example, stimuli that evoke lower-latency cortical potentials (e.g., more immediate peaks or latencies 802 that are closer to the left-hand side of the graph in FIG. 8) may be determined to be more optimal for the recipient than stimuli that evoke higher-latency cortical potentials (e.g., more delayed peaks or latencies 802 that are closer to the right-hand side of the graph in FIG. 8). As such, latencies 802 measured for cortical potentials 504 evoked by different stimuli may be used to quantify relative contributions of electric and acoustic components, and, in general, to optimize the mix between the electric and acoustic stimulation components. For example, the configuration that results in the smallest latency may indicate the least effort for the brain of the recipient and may thus be considered the most optimal.

In one example, these principles may be implemented by cochlear implant system 100 as follows. Processing unit 108 may detect a plurality of cortical potentials 504 that are produced by the recipient during a plurality of different fitting tests each employing a different fitting test configuration. Processing unit 108 may then determine a respective latency 802 for each of the plurality of cortical potentials 504 produced by the recipient during the plurality of different fitting tests. For instance, as shown, latencies 802-1 through 802-10 may coincide with when a particular peak is detected to arrive within the cortical potential evoked by each fitting test. Processing unit 108 may determine one or more fitting parameters 516 by determining a "best latency" of the respective latencies 802 determined for each of the plurality of cortical potentials. The best latency may be the latency 802 produced by the recipient during a particular fitting test of the plurality of different fitting tests. As such, and based on the determining of the best latency, processing unit 108 may select, as the one or more fitting parameters 516, one or more parameters used during the particular fitting test that resulted in the best latency. For example, whichever parameters were used in the configuration that produced the best latency may be determined to be suitable or the most optimized for future use of cochlear implant system 100 by the recipient and may therefore be selected for use in the future as parameters 516.

The "best latency" of the measured latencies 802 may be defined in any suitable way and the determination of whether a particular measured latency 802 is the "best" may be made in any manner as may serve a particular implementation. As one example, the "best" latency may be defined as a latency that first satisfies a particular latency threshold 804 as the respective latencies are being determined for each of the plurality of cortical potentials 504. In other words, the "best" latency may be the first latency of a tested configuration that satisfies (e.g., is less than) a particular latency threshold. As shown in FIG. 8, and assuming that the fitting tests are performed in order starting from the bottom (the fitting test associated with latency 802-1) and moving upward (up to the fitting test associated with latency 802-10), the first three fitting tests may each fail to produce a latency 802 that satisfies latency threshold 804 (i.e., since latencies 802-1 through 802-3 each fall to the right of latency threshold 804). The fourth fitting test, however, is shown to be the first one to produce a latency 802 (i.e., latency 802-4) that does satisfy latency threshold 804. Accordingly, latency 802-4 may be considered to be the "best latency" in this example when the best latency is defined in this way.

As another example, the "best" latency may be defined as a shortest latency 802 of the respective latencies 802 after all the respective latencies 802 have been determined for each of the plurality of cortical potentials 504. In other words, the "best" latency in these examples may only be determined after each of a plurality of configurations has been tested and the latency results are being compared to determine the lowest one. As shown in FIG. 8, regardless of what order the fitting tests are performed in, when all the tests have been performed it is the fitting test associated with latency 802-5 that produces the shortest latency of all. Accordingly, latency 802-5 may be considered to be the "best latency" in this example when the best latency is defined in this manner.

The stimulation applied to evoke cortical potentials 504 corresponding to the different fitting tests represented in FIGS. 7 and 8 may include tones of various frequencies and/or various broad-band noises, as well as unfiltered or filtered speech stimuli. As such, in certain examples, processing unit 108 may determine any of the fitting parameters 516 described herein as broadband parameters that are to be applied for every channel, while, in other examples, the fitting parameters 516 may be determined on a frequency-by-frequency or channel-by-channel basis. For example, T-level, M-level, loudness, and other thresholds described herein may be assessed for each of a variety of frequencies or frequency ranges.

To illustrate, FIG. 9 shows various sets of fitting parameters 516 that may be determined for different sound frequencies relevant to human hearing. Specifically, as shown in FIG. 9, a frequency scale 902 is shown to extend from approximately 20 Hz (i.e., the lowest frequency general perceivable by the human hear) to approximately 20 kHz (i.e., the highest frequency generally perceivable by the human ear). A plurality of sound frequencies 904 (e.g. sound frequencies or frequency ranges 904-1 through 904-9) are shown along frequency scale 902, each with several respective fitting parameters 516 associated with that sound frequency 904.

Processing unit 108 may perform the determining of fitting parameters 516 by determining respective sets 906 (e.g., sets 906-1 through 906-3) of fitting parameters 516. For example, a first set 906-1 of fitting parameters may include fitting parameters associated with a T-level, a second set 906-2 of fitting parameters may include fitting parameters associated with an M-level, a third set 906-3 of fitting parameters may include fitting parameters associated with a loudness threshold, and so forth for any of the fitting parameters described herein or as may serve a particular implementation. Within each set 906, a different fitting parameter 516 is shown to be associated with a different sound frequency 904. Accordingly, for example, rather than determining a single M-level to be employed by cochlear implant system 100 at all frequencies, this implementation may determine a set 906 of M-level fitting parameters 516 to be employed by cochlear implant system 100 to serve each of the various channels and/or sound frequencies 904 that the system covers.

Returning to FIG. 5, movement sensor 518 may be employed to mitigate and/or resolve certain issues that may arise as processing unit 108 determines fitting parameters 516 in certain of the ways that have been described. For example, when EEG fitting tests are performed using implanted electrodes 106 of cochlear implant system 100, certain artifacts may be present on cortical potentials 504 and/or on cortical potential data 514 as a result of movements made by the recipient as the cortical potentials were recorded. To deal with such artifacts, cochlear implant system 100 may include or be communicatively coupled with at least one motion sensor 518 such as an accelerometer or the like. Motion detected by motion sensor 518 may be used by processing unit 108 to help mitigate, correct, compensate for, and/or otherwise address unwanted artifacts on the EEG measurements.

For example, in one implementation, the detecting of cortical potentials 504 by cochlear implant system 100 may include detecting (e.g., using movement sensor 518) a movement of the recipient as a raw cortical potential is measured, and determining (e.g., by processing unit 108) that the movement of the recipient results in an artifact in the raw cortical potential. The detecting may then include altering the raw cortical potential to compensate for the artifact prior to the detected cortical potential 504 being used as a basis for the determining of any fitting parameters 516.

As another example, in the same or other implementations, the detecting of cortical potentials 504 by cochlear implant system 100 may include tracking (e.g., using movement sensor 518) movements of the recipient prior to cortical potentials 504 being measured, and determining that the tracked movements of the recipient satisfy a movement threshold. For example, the movement threshold may be satisfied only when the recipient's movements are at a minimum (i.e., when the recipient is relatively still). The detecting may include measuring cortical potentials 504 in response to the determining that the tracked movements satisfy the movement threshold. In other words, motion sensors 518 may indicate when the recipient is holding relatively still such that EEG tests or other fitting tests may be performed with a low risk of unwanted artifacts being present in the test results.

Figure 10A:
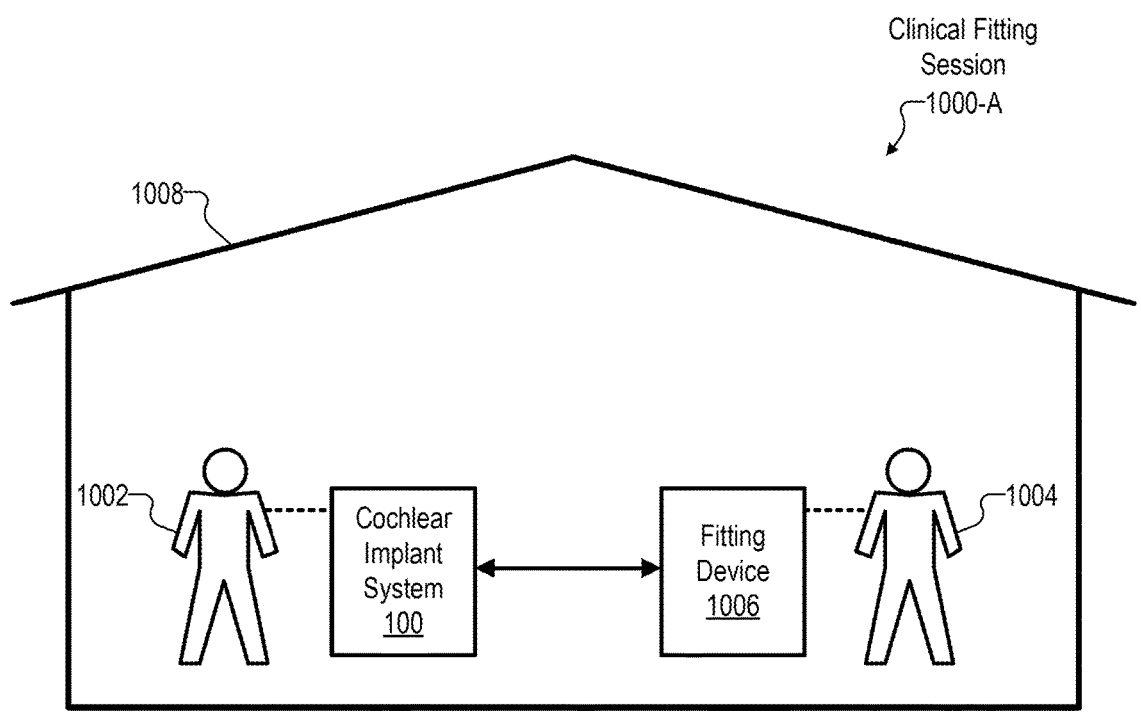
FIGS. 10A and 10B show illustrative fitting sessions during which a hearing system may be fitted to a recipient based on cortical potentials of the recipient.
Figure 10B:
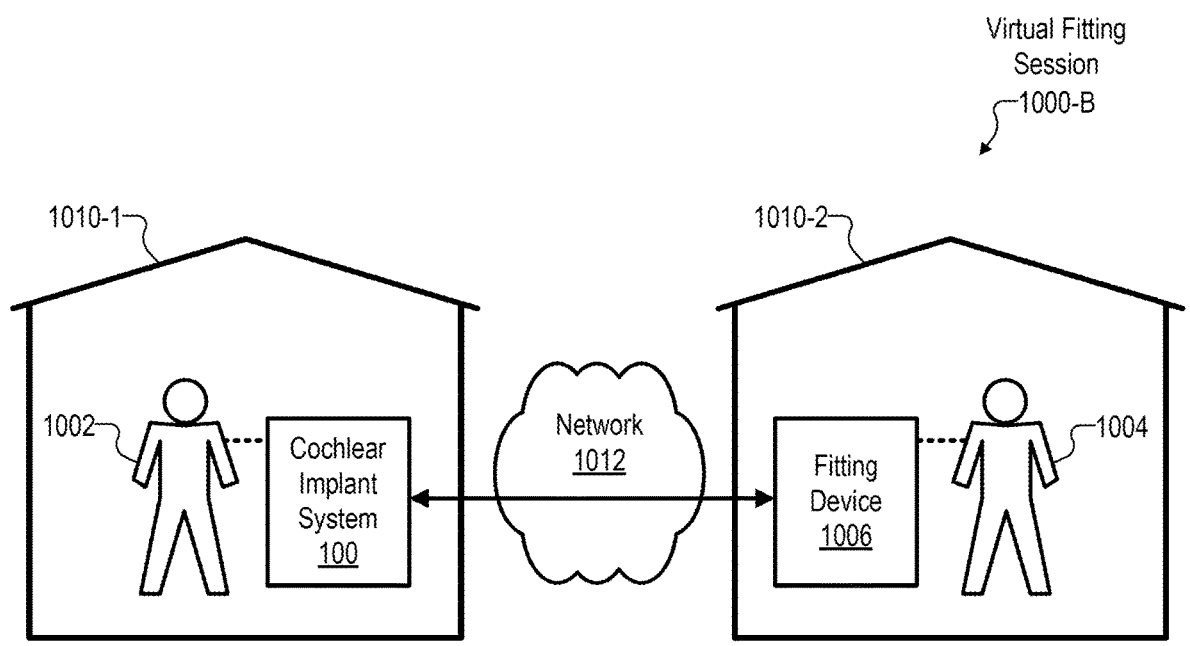

FIGS. 10A and 10B show illustrative fitting sessions 1000 (e.g., sessions 1000-A and 1000-B) during which a hearing system such as an implementation of cochlear implant system 100 may be fitted to a recipient based on cortical potentials of the recipient. Specifically, as shown, FIG. 10A illustrates a clinical fitting session 1000-A in which a recipient 1002 of an implementation of cochlear implant system 100 undergoes fitting procedures administered by a clinician 1004 using a fitting device 1006 while both recipient 1002 and clinician 1004 are co-located together at a single site 1008 (e.g., at a hearing clinic or the like).

Clinical fitting sessions such as session 1000-A where recipient 1002 and clinician 1004 are co-located may be scheduled periodically to allow clinician 1004 to check in on recipient 1002 in person and to monitor his or her progress with respect to cochlear implant system 100. Cochlear implant system 100, fitting device 1006 (which may implement computer device 302 in certain examples), and/or other technology may assist in tracking the progress of recipient 1002 in any suitable way. For example, cochlear implant system 100 may be configured detect cortical potentials produced by the recipient during different fitting sessions 1000 over a period of time (e.g., over several months, several years, etc.). Based on these detected cortical potentials, cochlear implant system 100 may track a progress of recipient 1002 over the period of time and provide (e.g., to clinician 1004 by way of fitting device 1006) an indication of the tracked progress of the recipient over the period of time.

In some examples, the tracked progress may be based on the detection of P3 peaks over time (e.g., from fitting session 1000 to fitting session 1000, etc.) to determine if a particular recipient is progressing in a rehabilitation regime or if the progression of the recipient is insufficient (e.g., below a threshold, etc.). Upon making such a determination, cochlear implant system 100 may be configured to provide input regarding the progress (e.g., a warning, etc.) to recipient 1002 and/or to clinician 1004. In some examples, cochlear implant system 100 may provide a visual display of P3 peaks during or subsequent to clinical fitting sessions such as session 1000-A to help recipient 1002 and clinician 1004 track the recipient's development and progress. For example, such a visual display may be provided to a mobile device of recipient 1002, to fitting device 1006 of clinician 1004, to another implementation of computing device 302, or to another suitable display device.

Additionally or alternatively, the tracked progress may be based on a detection and analysis of binaural interaction components ("BICs") associated with bilateral hearing systems (e.g., bilateral cochlear implant systems, bimodal hearing systems, etc.). BICs may serve as a particular type of cortical potential that indicate the extent to which both sides of the bilateral hearing system are engaging with one another. In other words, a BIC measurement may indicate the difference between how a recipient benefits from a bilateral hearing system as compared to how the recipient would benefit from only the sum of the unilateral left and right hearing systems. Accordingly, cochlear implant system 100 may use BIC measurements to optimize interaural time difference ("ITD") and/or interaural level difference ("ILD") alignment among electrodes and levels. As with the P3 peak tracking described above, progress related to BIC measurements for recipient 1002 may be tracked and displayed using a mobile device of recipient 1002, fitting device 1006 of clinician 1004, or another suitable device.

In still other examples, the tracked progress may be based on auditory ERPs used to monitor a cortical phase synchrony (inter-trial coherence ("ITC")) after a recipient is treated with cochlear implant system 100. Recipients such as deaf children, children with auditory neuropathy, and so forth, may typically exhibit a reduced ITC. Fortunately, cochlear implant implantation may help improve ITC, and improvements in cortical phase synchrony may serve as an objective marker of benefit from treatment. If improvements are not achieved, cochlear implant system 100 may indicate to clinician 1004 that changes in the cochlear implant system program should be recommended or implemented (e.g. by increasing levels, by prescribing an electroacoustic hearing system rather than a cochlear implant system, etc.). To this end, cochlear implant system 100 may perform a time-frequency decomposition of a recorded EEG cortical signal and compute the phase synchronization across trials. Hypothetically, this synchrony should improve over the course of cochlear implant use (e.g., particularly in neuropathy subjects, because the cochlear implant is providing strong electrical stimulation that is driving more robust and synchronous firing along the central auditory pathway). As with the P3 peak and BIC tracking described above, progress related to cortical phase synchrony measurements for recipient 1002 may be tracked and displayed using a mobile device of recipient 1002, a fitting device 1006 of clinician 1004, or another suitable device.

In contrast to clinical fitting session 1000-A of FIG. 10A, where recipient 1002 and clinician 1004 are co-located at site 1008 for the fitting session, FIG. 10B illustrates a virtual fitting session 1000-B during which recipient 1002 undergoes fitting procedures that are automatically administered or remotely overseen by clinician 1004 while recipient 1002 and clinician 1004 are not co-located at a single site. Specifically, as shown, during virtual fitting session 1008-B, recipient 1002 and cochlear implant system 100 may be located at a first site 1010-1 (e.g., the recipient's home, etc.), clinician 1004 and fitting device 1006 may be located at a second, different site 1010-2 (e.g., the hearing clinic, etc.), and cochlear implant system 100 may be remotely coupled to fitting device 1006 by way of a network 1012. In certain examples (not explicitly shown), cochlear implant system 100 and fitting device 1006 may not be communicatively coupled to one another during virtual fitting session 1000-B. For instance, as described above, cochlear implant system 100 may automatically perform fitting procedures, in certain examples, without direction from fitting device 1006 or clinician 1004.

As shown in FIG. 10B, the detecting of the cortical potentials (e.g., cortical potentials 504) and the determining of the fitting parameters based on the detected cortical potentials (e.g., fitting parameters 516) may be performed as part of virtual fitting session 1000-B during which the recipient is located at a first location (e.g., site 1010-1) that is different from a second location (e.g., site 1010-2) at which clinician 1004 overseeing virtual fitting session 1000-B is located. In some implementations, it may be determined that it is undesirable for virtual fitting session 1000-B to take place under certain circumstances. For example, if recipient 1002 is away from home (e.g., at work, driving to another location, engaged in a social interaction, etc.), it may be undesirable for a virtual fitting session to be initiated due to distractions that the fitting session could cause for recipient 1002. Accordingly, prior to initiating virtual fitting session 1000-B, cochlear implant system 100 may be configured to determine the first location at which the recipient is located, determine that the first location is an approved location for the recipient to be located during the virtual fitting session (e.g., determine if site 1010-1 where recipient 1002 is located is the home of recipient 1002 or another approved location, etc.), and initiate virtual fitting session 1000-B based on the determining that the first location is an approved location.

The determining of the location at which the recipient is located and whether the location is approved may be performed in any suitable way. For example, a global positioning system ("GPS") sensor associated with cochlear implant system 100 or recipient 1002 (e.g., built in to a mobile device carried by recipient 1002 and communicatively coupled to cochlear implant system 100) may indicate the recipient's current geolocation in certain implementations. Additionally, measurement from a microphone of cochlear implant system 100 (e.g., microphone 204) may be used to determine whether the time is appropriate for a virtual fitting session. For example, if the microphone signal level is low and no speech information is present, it may be determined (in combination with geolocation) that it is a suitable time for the virtual fitting session.

Virtual fitting sessions such as session 1000-B may provide various advantages and conveniences that are not provided by conventional clinical fitting sessions such as session 1000-A. For example, virtual fitting session 1000-B may remove the need for recipient 1002 and/or his or her caretaker (e.g., parent in the case of a child recipient, etc.) to set an appointment for the session, to drive in to the clinic at a particular time to keep the appointment, and so forth. Moreover, virtual fitting sessions such as session 1000-B may be performed more frequently than clinical fitting sessions such as session 1000-A to provide more optimized and updated fitting parameters, more detailed and accurate progress tracking, and so forth.

In the preceding description, various illustrative embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant system comprising:
   an electrode lead having an array of electrodes;
   a cochlear implant coupled with the electrode lead and configured to be implanted within a recipient together with the electrode lead; and
   a processing unit communicatively coupled to the cochlear implant and configured to:
      direct the cochlear implant to apply stimulation to the recipient by way of the array of electrodes during a plurality of different fitting tests each employing a different fitting test configuration,
      detect, by way of one or more electrodes included in the array of electrodes, a plurality of cortical potentials produced by the recipient in response to the stimulation during the plurality of different fitting tests,
      determine a respective latency for each of the plurality of cortical potentials produced by the recipient during the plurality of different fitting tests,
      determine a best latency of the respective latencies determined for each of the plurality of cortical potentials, the best latency associated with a particular cortical potential included in the plurality of cortical potentials and produced by the recipient during a particular fitting test of the plurality of different fitting tests, and
      selecting, based on the determining of the best latency, a parameter used during the particular fitting test as a fitting parameter associated with the cochlear implant system.

2. The cochlear implant system of claim 1, wherein the fitting parameter is at least one of:
   an M-level value representative of a most comfortable sound level for the recipient;
   a T-level value representative of a softest sound level the recipient is capable of perceiving; or
   a loudness threshold representative of an upper comfort level at which the recipient perceives sound as uncomfortably loud.

3. The cochlear implant system of claim 1, wherein:
   the processing unit is further configured to direct test stimulation to be applied to the recipient;
   the particular cortical potential is an evoked potential produced by the recipient in response to the test stimulation; and
   the test stimulation is implemented by at least one of:
      the stimulation applied to the recipient by way of the array of electrodes, or
      acoustic stimulation applied to the recipient by a loudspeaker directed by the processing unit.

4. The cochlear implant system of claim 3, wherein:
   the cochlear implant system is included within a bimodal hearing system together with a hearing aid system employed contralaterally to the cochlear implant system on a different ear of the recipient than the cochlear implant system;
   the test stimulation is implemented by the acoustic stimulation; and
   the loudspeaker is included within the hearing aid system and is configured to provide the acoustic stimulation when directed by the processing unit.

5. The cochlear implant system of claim 3, wherein:
   the test stimulation is implemented by the acoustic stimulation; and
   the cochlear implant system is implemented as an electroacoustic hearing system that further comprises the loudspeaker that applies the acoustic stimulation to the recipient when directed by the processing unit.

6. The cochlear implant system of claim 1, wherein:
   the fitting parameter includes a first fitting parameter and a plurality of additional fitting parameters;
   the fitting parameter is associated with a first sound frequency; and
   the additional fitting parameters are associated with respective sound frequencies different from the first sound frequency.

7. The cochlear implant system of claim 1, wherein:
   the processing unit is further configured to determine that a behavioral fitting methodology and an electrocochleographic (ECochG) fitting methodology are both unavailable for determining the fitting parameter; and
   the detecting of the plurality of cortical potentials and the selecting of the parameter used during the particular fitting test as the fitting parameter based are performed in response to the determining that the behavioral and ECochG fitting methodologies are both unavailable for determining the fitting parameter.

8. The cochlear implant system of claim 1, wherein the detecting of the plurality of cortical potentials is performed under direction of a user performing a fitting procedure with respect to the cochlear implant system and the recipient.

9. The cochlear implant system of claim 1, wherein:
   the processing unit is further configured to perform an electroencephalography (EEG) test using one or more electrodes included in the array of electrodes; and
   the detecting of the plurality of cortical potentials is performed as part of the EEG test.

10. The cochlear implant system of claim 1, wherein the best latency is defined as a latency that first satisfies a particular threshold as the respective latencies are being determined for each of the plurality of cortical potentials.

11. The cochlear implant system of claim 1, wherein the best latency is defined as a shortest latency of the respective latencies after all the respective latencies have been determined for each of the plurality of cortical potentials.

12. The cochlear implant system of claim 1, wherein:
   the particular cortical potential produced by the recipient indicates that the recipient perceives acoustic stimulation that has evoked the particular cortical potential;

the processing unit is further configured to provide, based on the particular cortical potential indicating that the recipient perceives the acoustic stimulation, a recommendation that a hearing system that applies both electrical and acoustic stimulation is to be used by the recipient.

13. The cochlear implant system of claim 1, wherein the processing unit is further configured to:
    detect, during different sessions over a period of time, additional cortical potentials produced by the recipient;
    track, based on the particular cortical potential and additional cortical potentials, a progress of the recipient over the period of time; and
    provide an indication of the tracked progress of the recipient over the period of time.

14. The cochlear implant system of claim 1, wherein the detecting of the particular cortical potential includes:
    detecting a movement of the recipient as a raw cortical potential is measured;
    determining that the movement of the recipient results in an artifact in the raw cortical potential; and
    altering the raw cortical potential to compensate for the artifact prior to the particular cortical potential being used as a basis for the determining of the fitting parameter.

15. The cochlear implant system of claim 1, wherein the detecting of the particular cortical potential includes:
    tracking movements of the recipient prior to the particular cortical potential being measured;
    determining that the tracked movements of the recipient satisfy a movement threshold; and
    measuring the particular cortical potential in response to the determining that the tracked movements satisfy the movement threshold.

16. The cochlear implant system of claim 1, wherein the detecting of the plurality of cortical potentials and the selecting the parameter used during the particular fitting test as the fitting parameter are performed as part of a virtual fitting session during which the recipient is located at a first location that is different from a second location at which a clinician overseeing the virtual fitting session is located.

17. The cochlear implant system of claim 16, wherein the processing unit is further configured, prior to initiating the virtual fitting session, to:
    determine the first location at which the recipient is located;
    determine that the first location is an approved location for the recipient to be located during the virtual fitting session; and
    initiate the virtual fitting session based on the determining that the first location is an approved location.

18. A method comprising:
    directing, by a cochlear implant system including a cochlear implant and an electrode lead having an array of electrodes, the cochlear implant to apply stimulation to a recipient by way of the array of electrodes during a plurality of different fitting tests each employing a different fitting test configuration;
    detecting, by the cochlear implant system and by way of one or more electrodes included in the array of electrodes, a plurality of cortical potentials produced by the recipient in response to the stimulation during the plurality of different fitting tests;
    determining, by the cochlear implant system, a respective latency for each of the plurality of cortical potentials produced by the recipient during the plurality of different fitting tests;
    determining, by the cochlear implant system, a best latency of the respective latencies determined for each of the plurality of cortical potentials, the best latency associated with a particular cortical potential included in the plurality of cortical potentials and produced by the recipient during a particular fitting test of the plurality of different fitting tests; and
    selecting, by the cochlear implant system based on the determining of the best latency, a parameter used during the particular fitting test as a fitting parameter associated with the cochlear implant system.

19. A system comprising:
    a memory storing instructions; and
    a processor communicatively coupled to the memory and configured to execute the instructions to:
        direct a cochlear implant included within a cochlear implant system to apply stimulation to a recipient of the cochlear implant system by way of an array of electrodes included on an electrode lead within the cochlear implant system;
        detect, by way of one or more electrodes included in the array of electrodes, a cortical potential produced by the recipient in response to the stimulation;
        determine a latency of the cortical potential; and
        determine, based on the latency of the cortical potential, a fitting parameter associated with the cochlear implant system.

\* \* \* \* \*